(12) United States Patent
Takahashi et al.

(10) Patent No.: US 8,075,722 B2
(45) Date of Patent: Dec. 13, 2011

(54) METHOD OF MANUFACTURING ELASTIC SHEET, AND ELASTIC SHEET AND ABSORBENT PRODUCT

(75) Inventors: Yuki Takahashi, Mima-gun (JP); Hironobu Yokokawa, Mima-gun (JP); Masaru Fujioka, Mima-gun (JP)

(73) Assignee: Livedo Corporation, Ehime (JP)

( * ) Notice: Subject to any disclaimer, the term of this patent is extended or adjusted under 35 U.S.C. 154(b) by 631 days.

(21) Appl. No.: 12/153,676

(22) Filed: May 22, 2008

(65) Prior Publication Data

US 2008/0300565 A1 Dec. 4, 2008

(30) Foreign Application Priority Data

May 30, 2007 (JP) ................ P2007-143495

(51) Int. Cl.
*B32B 37/00* (2006.01)
*B32B 38/04* (2006.01)

(52) U.S. Cl. ........ 156/253; 156/161; 156/176; 156/177; 156/179; 156/229; 156/252; 156/256; 156/257; 156/269; 156/270

(58) Field of Classification Search .......... 156/252, 156/253, 257, 269, 270, 256, 161, 177, 176, 156/179, 229
See application file for complete search history.

(56) References Cited

U.S. PATENT DOCUMENTS

| | | | |
|---|---|---|---|
| 3,404,607 A * | 10/1968 | Feick et al. ............ | 493/373 |
| 5,622,581 A | 4/1997 | Ducker et al. | |
| 6,391,013 B1 * | 5/2002 | Suzuki et al. ............ | 604/385.27 |
| 2002/0007172 A1 | 1/2002 | Takei et al. | |
| 2002/0046802 A1 | 4/2002 | Tachibana et al. | |
| 2004/0016500 A1 | 1/2004 | Tachibana et al. | |
| 2004/0133180 A1 | 7/2004 | Mori et al. | |
| 2004/0230171 A1 | 11/2004 | Ando et al. | |
| 2005/0004549 A1 | 1/2005 | Maas et al. | |
| 2006/0254698 A1 | 11/2006 | Tachibana et al. | |
| 2007/0043331 A1 * | 2/2007 | Haruki et al. ............ | 604/385.3 |
| 2009/0283207 A1 | 11/2009 | Tachibana et al. | |

FOREIGN PATENT DOCUMENTS

EP 0 626 161 11/1994

(Continued)

OTHER PUBLICATIONS

European Search Report (in English language) issued Oct. 29, 2008.

*Primary Examiner* — Linda L Gray

(74) *Attorney, Agent, or Firm* — Wenderoth, Lind & Ponack, L.L.P.

(57) ABSTRACT

In a manufacturing apparatus of an absorbent product, extended elastic yarns to be a first middle elastic member and extended elastic yarns to be leg elastic members are bonded between a first sheet and a second sheet and arranged crossing each other in manufacturing an outer covering sheet. A first middle elastic member and an inclined part of the leg elastic members crossing the first middle elastic member are simultaneously and reliably cut in a crossing area of the both elastic members by first cutting blades tilted relatively to a direction where the first middle elastic member is positioned and second cutting blades tilted relatively to a direction where the inclined part is positioned. Thus, it is possible to easily form the outer covering sheet which maintains elasticity in a required portion and has high flexibility.

7 Claims, 10 Drawing Sheets

FOREIGN PATENT DOCUMENTS

| | | |
|---|---|---|
| EP | 1 761 224 | 11/2007 |
| JP | 2000-140021 | 5/2000 |
| JP | 2002-113042 | 4/2002 |
| JP | 2002-273808 | 9/2002 |
| JP | 2005-278774 | 10/2005 |
| JP | 2006-122456 | 5/2006 |

* cited by examiner

METHOD OF MANUFACTURING ELASTIC SHEET, AND ELASTIC SHEET AND ABSORBENT PRODUCT

BACKGROUND OF THE INVENTION

1. Field of the Invention

The present invention relates to an elastic sheet which is a part of an absorbent product for receiving excrement from a wearer, and to a method of manufacturing the elastic sheet, and also relates to an absorbent product having the elastic sheet.

2. Description of the Background Art

In an absorbent product such as a disposal diaper (i.e. a disposable diaper) for receiving excrement from a wearer, elasticity has been conventionally applied to various portions in order to improve fitting to the wearer or improve an appearance of the absorbent product. For example, in a pants-type disposal diaper, waist opening gathers, leg opening gathers and the like with elasticity are provided, and elasticity is also applied to a front part and a back part located on a stomach side and a back side of the wearer.

A pants-type absorbent product in Japanese Patent Application Laid-Open No. 2000-140021 (Document 1) discloses a technique for favorably fitting an absorbent to a crotch part of a wearer, where a plurality of absorbent part elastic members which are linearly arranged in parallel with a direction perpendicular to a longitudinal direction of an absorbent core are disposed on a back sheet between right and left leg opening edges at a position corresponding to the crotch part, with crossing the absorbent core and leg elastic members on right and left sides of the absorbent core.

Japanese Patent Application Laid-Open No. 2006-122456 (Document 2) discloses a pants-type paper diaper where a rectangular sheet part is attached on each of end portions in a longitudinal direction of an absorbent, and right and left ends of two sheet parts are bonded to form the paper diaper. In the paper diaper, it is proposed that a plurality of first rubber threads which are arranged almost in parallel with a direction of waistline of a wearer (i.e., a horizontal direction) and a plurality of second rubber threads which are arranged so as to cross the first rubber threads, are provided in each of the sheet parts facing the waistline, and thereby the sheet parts contract not only in the direction of the waistline but also in a direction crossing the direction of the waistline, to improve fitting around wearer's legs.

In the absorbent products of Documents 1 and 2, however, since elastic members extending in different directions cross in the vicinity of leg openings, there is a possibility that a sheet member close to a crossing part contracts in two directions to become rigid and the legs of the wearer are strongly compressed. Flexibility in the vicinity of the leg openings is decreased and the legs of the wearer might not be smoothly inserted into the leg openings in wearing the absorbent product, which decreases the comfort of the wearer. Further, in the pants-type paper diaper of Document 2, since the elastic members cross in portions overlapping with the absorbent, twist of the absorbent occurs.

SUMMARY OF THE INVENTION

The present invention is a method of manufacturing an elastic sheet which is a part of an absorbent product for receiving excrement from a wearer. It is an object of the present invention to easily form the elastic sheet with high flexibility.

The method of manufacturing an elastic sheet comprises the steps of: a) positioning an extended first elastic member along a first direction on a first sheet member which is transferred in a transfer direction, positioning an extended second elastic member along a second direction tilted relatively to the first direction and crossing the first elastic member, laminating a second sheet member on the first sheet member with interposing the first elastic member and the second elastic member between the first sheet member and the second sheet member, and bonding the first sheet member and the second sheet member with each other; and b) cutting the first elastic member and the second elastic member in a crossing area of the first elastic member and the second elastic member together with at least one of the first sheet member and the second sheet member, by cutting blades which include a plurality of first cutting blades tilted relatively to the first direction and a plurality of second cutting blades tilted relatively to the second direction. It is thereby possible to easily form an elastic sheet with high flexibility.

According to a preferred embodiment of the present invention, the first elastic member has a plurality of first elastic yarns along the first direction, and the second elastic member has a plurality of second elastic yarns along the second direction.

According to another preferred embodiment of the present invention, the cutting blades include: the plurality of first cutting blades tilted relatively to the first direction at an angle which is equal to or larger than 45 degrees and equal to or smaller than 135 degrees; and the plurality of second cutting blades tilted relatively to the second direction at an angle which is equal to or larger than 45 degrees and equal to or smaller than 135 degrees. With this operation, it is possible to reliably cut both of the first elastic member and the second elastic member. More preferably, the plurality of first cutting blades are tilted relatively to the first direction at an angle which is equal to or larger than 80 degrees and equal to or smaller than 100 degrees, and the plurality of second cutting blades are tilted relatively to the second direction at an angle which is equal to or larger than 80 degrees and equal to or smaller than 100 degrees. A plurality of cutting lines formed by the plurality of first cutting blades and a plurality of cutting lines formed by the plurality of second cutting blades are uniformly distributed in the crossing area of the first elastic member and the second elastic member in the step b).

According to still another preferred embodiment of the present invention, the first direction is parallel to the transfer direction.

The present invention is also intended for an elastic sheet which is a part of an absorbent product for receiving excrement from a wearer. The elastic sheet comprises: a first sheet; a second sheet which is laminated on the first sheet to be bonded with the first sheet; a first elastic member positioned along a first direction between the first sheet and the second sheet, bonded with the first sheet and the second sheet, and contracting the first sheet and the second sheet; and a second elastic member positioned along a second direction which is tilted relatively to the first direction between the first sheet and the second sheet with crossing the first elastic member, bonded with the first sheet and the second sheet, and contracting the first sheet and the second sheet, and in a state where the first sheet and the second sheet are expanded, at least one of the first sheet and the second sheet has cutting lines which include a plurality of first cutting lines tilted relatively to the first direction in a crossing area of the first elastic member and the second elastic member and a plurality of second cutting lines tilted relatively to the second direction in the crossing area, the first elastic member and the second elastic member are cut at positions of the plurality of cutting lines, and an area where the plurality of cutting lines exist is a non-contracted part. It is thereby possible to maintain elasticity in a required portion and improve flexibility of the elastic sheet.

The present invention is still also intended for a pants-type absorbent product which has a waist opening at an upper end and a pair of leg openings on a lower part. The absorbent product comprises: an outer covering sheet folded in a middle part which is a lower part between a front part and a back part to be positioned on a stomach side and a back side of a wearer, right and left ends of the front part being bonded to right and left ends of the back part, respectively, to form a waist opening at upper ends of the front part and the back part and a pair of leg openings on right and left sides of the middle part; and an absorbent which is attached on an inner side of the outer covering sheet to absorb excrement from the wearer, and in the absorbent product, the outer covering sheet includes the above-discussed elastic sheet, and the first elastic member in the elastic sheet is one of a waist elastic member which is located along an edge of the waist opening and contracts to form waist opening gathers, leg elastic members which are located along edges of the pair of leg openings, respectively, and contract to form a pair of leg opening gathers, a front elastic member which is located on the front part along a horizontal direction between the waist elastic member and the leg elastic members and contracts to form front gathers, a back elastic member which is located on the back part along the horizontal direction between the waist elastic member and the leg elastic members and contracts to form back gathers, and a middle elastic member which is located along the horizontal direction on the middle part between the pair of leg openings and contracts to form middle gathers. It is thereby possible to maintain elasticity in a required portion and improve flexibility of the absorbent product.

These and other objects, features, aspects and advantages of the present invention will become more apparent from the following detailed description of the present invention when taken in conjunction with the accompanying drawings.

DETAILED DESCRIPTION OF THE INVENTION

Figure 1:
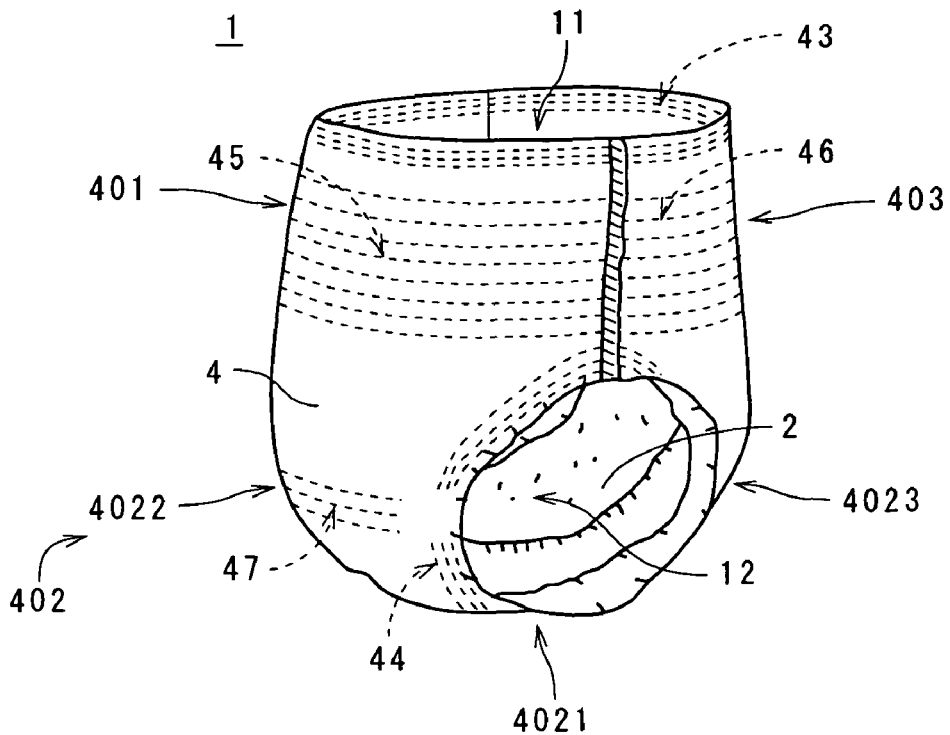
FIG. 1 is a perspective view showing an appearance of an absorbent product in accordance with the first preferred embodiment.
Figure 2:
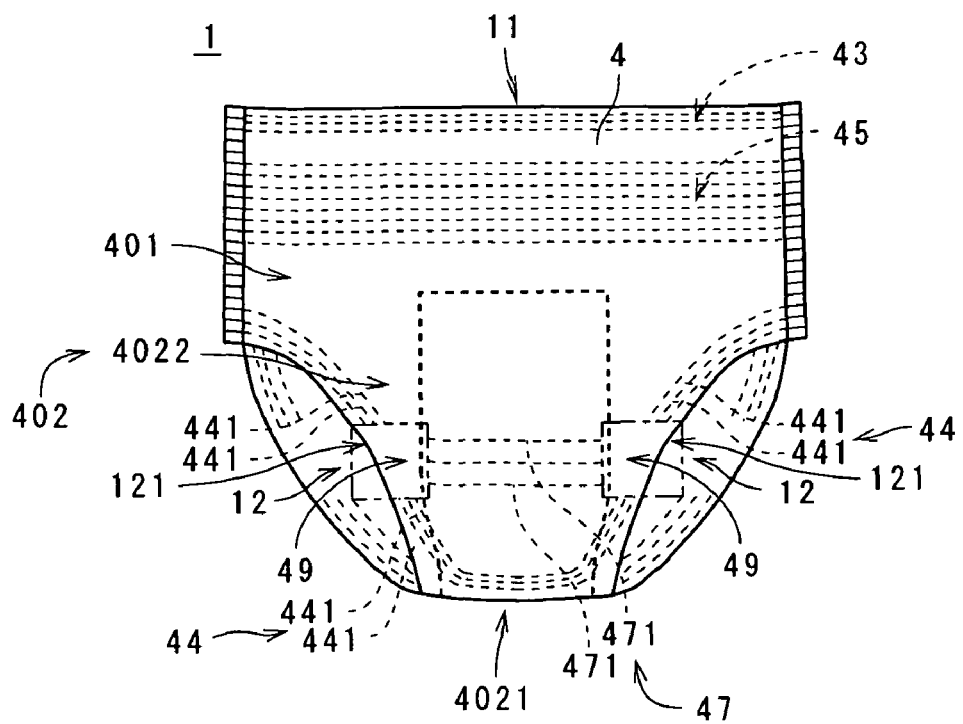
FIG. 2 is a front view of the absorbent product.
Figure 3:
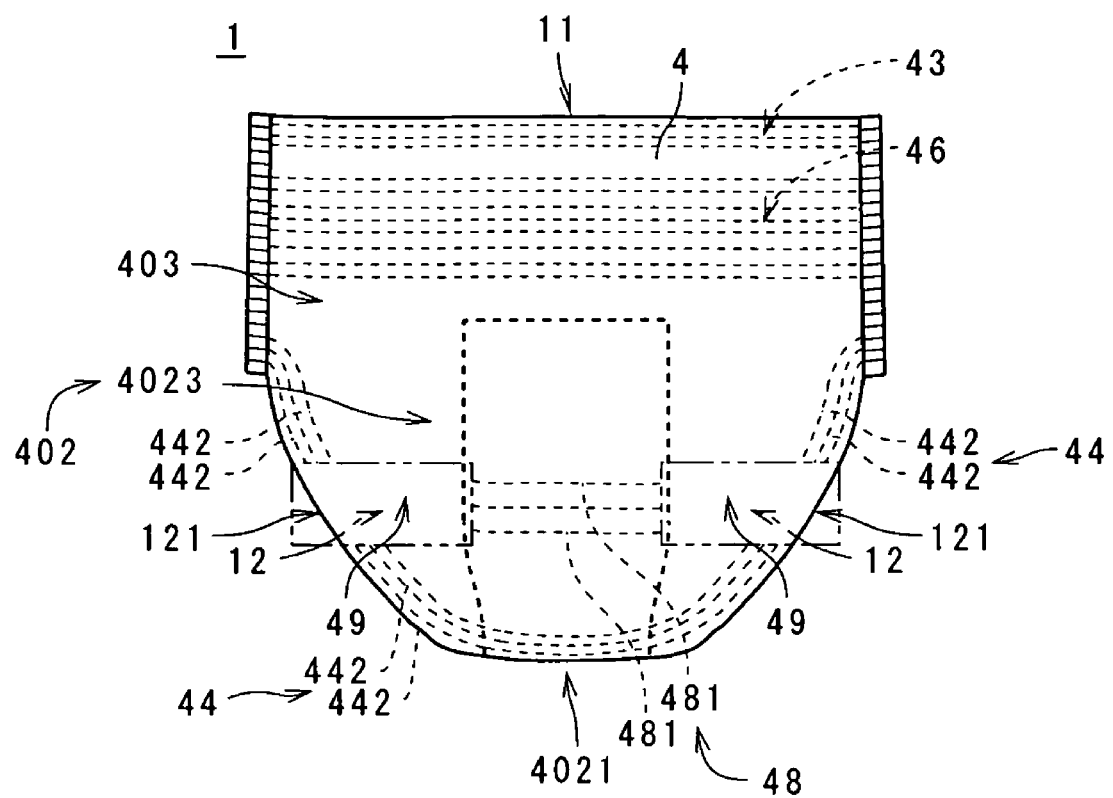
FIG. 3 is a rear view of the absorbent product.

FIG. 1 is a perspective view showing an appearance of an absorbent product 1 in accordance with the first preferred embodiment of the present invention. FIG. 2 is a front view (i.e., view of a portion to be positioned on a stomach side (an abdomen) of a wearer) of the absorbent product 1 and FIG. 3 is a rear view (i.e., view of a portion to be positioned on a back side (a back) of the wearer) of the absorbent product 1. As shown in FIGS. 1 to 3, the absorbent product 1 is a pants-type (i.e., pull-up type) disposal diaper which has a waist opening 11 at an upper end (i.e., an end on the upper side of FIG. 1) and a pair of leg openings 12 on a lower part.

Figure 4:
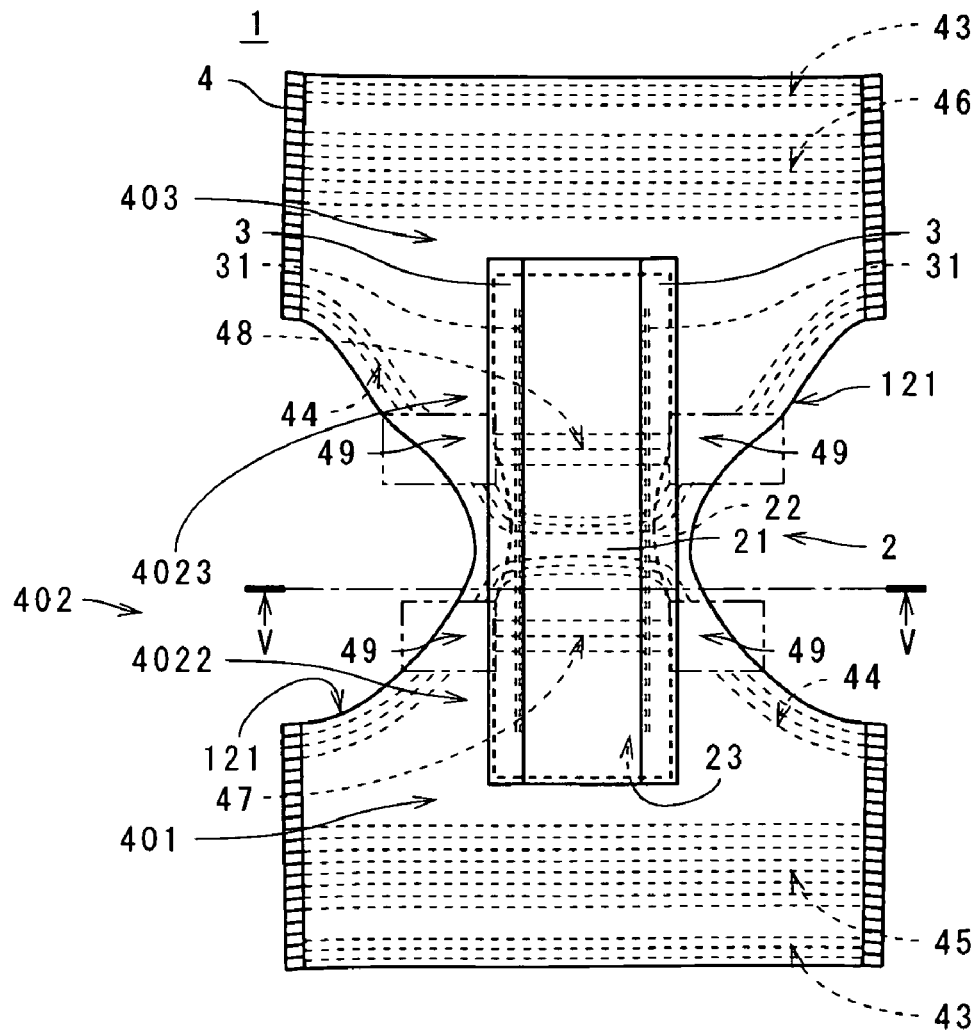
FIG. 4 is a plan view of the absorbent product in a state where the absorbent product is spread.

FIG. 4 is a plan view of the absorbent product 1 as viewed from the wearer's side in a state where the absorbent product 1 is spread. As shown in FIG. 4, the absorbent product 1 has an almost sheet-like outer covering sheet 4 and an absorbent 2 which is attached on an inner side of the outer covering sheet 4 to absorb excrement from the wearer. In the absorbent product 1, a lower portion 401 in FIG. 4 of the outer covering sheet 4 is to be positioned on the stomach side of the wearer, and an upper portion 403 in FIG. 4 is to be positioned on the back side of the wearer. In the following description, the portions 401, 403 which are to be positioned on the stomach side and the back side of the wearer in the outer covering sheet 4 are referred to as a "front part 401" and a "back part 403", respectively, and a portion 402 to come into contact with a crotch region of the wearer between the front part 401 and the back part 403 is referred to as a "middle part 402".

As shown in FIG. 1, in the absorbent product 1, the outer covering sheet 4 is folded in a folded part 4021 which is a lower end of the middle part 402, together with the absorbent 2. Right and left ends of the front part 401 (i.e., both ends in a width direction of the front part 401) are bonded to right and left ends of the back part 403 (i.e., both ends in the width direction of the back part 403), respectively. Thus, the waist opening 11 is formed at upper ends of the front part 401 and the back part 403 and a pair of leg openings 12 are formed on right and left sides of the middle part 402, to thereby form the absorbent product 1 in a shape of underpants. In the following description, a portion between the front part 401 and the folded part 4021 of the middle part 402 is referred to as a "middle front part 4022" and a portion between the back part 403 and the folded part 4021 of the middle part 402 is referred to as a "middle back part 4023".

Figure 5:
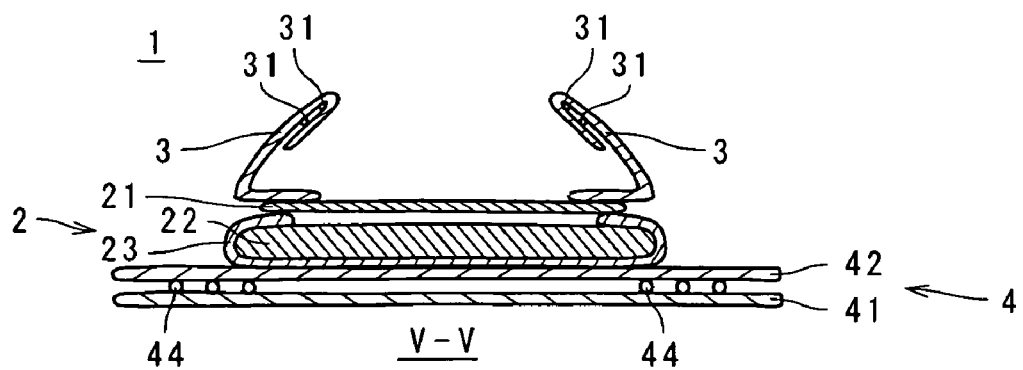
FIG. 5 is a cross-sectional view of the absorbent product.

FIG. 5 is a cross-sectional view of the absorbent product 1 taken along a line V-V in FIG. 4. As shown in FIGS. 4 and 5, the absorbent 2 has an absorbent core 22, a top sheet 21 covering an upper surface of the absorbent core 22 (i.e., one main surface on an inner side of the absorbent core 22), a back sheet 23 covering a lower surface of the absorbent core 22 (i.e., the other main surface of the absorbent core 22), and a pair of side wall parts 3 which are provided over an almost entire length in a longitudinal direction of the absorbent core 22 on right and left sides in the width direction (i.e., horizontal direction) of the absorbent core 22 (i.e., the longitudinal direction is a vertical direction in FIG. 4 and corresponds to a longitudinal direction of the absorbent product 1, and the width direction is perpendicular to the longitudinal direction of the absorbent core 22). The contour of the absorbent core 22 is shown by a thick broken-line in FIG. 4. The top sheet 21 and the back sheet 23 are bonded with each other around the absorbent core 22 by hot melt adhesive or the like, and the side wall part 3 is bonded to each side of the absorbent core 22. In FIG. 5, a space is provided between the top sheet 21 and the absorbent core 22 for convenience of illustration.

The top sheet 21 is a nonwoven fabric made of liquid-pervious material, for example, hydrophilic fiber, and the top sheet 21 immediately catches moisture of excrement from the wearer and moves the moisture into the absorbent core 22. Examples of the nonwoven fabric used for the top sheet 21 are a point-bond nonwoven fabric, air-through nonwoven fabric, or spunlace nonwoven fabric, and as hydrophilic fibers for making these nonwoven fabrics, normally, cellulose, rayon, cotton or the like are used. As the top sheet 21, a liquid-pervious nonwoven fabric made of hydrophobic fiber (for example, polypropylene, polyethylene, polyester, polyamide, or nylon) on which hydrophilic treatment is performed with a surfactant may be utilized or a microporous plastic film may be used.

The absorbent core 22 is formed by wrapping a mixture of hydrophilic fibers (e.g., crushed pulp fibers or cellulose fibers) and granulated absorbent polymers (e.g., SAP (Super Absorbent Polymer)) in a cover sheet such as a tissue paper or a liquid-penetrable nonwoven fabric, and the absorbent core 22 rapidly absorbs and retains moisture passing through the top sheet 21. The cover sheet is bonded to the hydrophilic fibers and the absorbent polymers with the hot melt adhesive, to prevent deformation of the hydrophilic fibers and falling of the absorbent polymers (especially, falling after absorption of moisture).

The back sheet 23 is a water-repellent or liquid-impervious plastic film, and the back sheet 23 prevents the moisture which has passed through the top sheet 21 and the moisture which is retained in the absorbent core 22 from leaking out into the outer covering sheet 4. From the view point of comfort for wearer, it is preferable a plastic film with breathability is used as the back sheet 23. As the back sheet 23, a water-repellent or liquid-impervious nonwoven fabric or a laminated sheet in which a water-repellent or liquid-impervious plastic film is laminated on an inner side of the water-repellent or liquid-impervious nonwoven fabric can be used. Nonwoven fabrics used for the back sheet 23 are, for example, a spunbond nonwoven fabric, a meltblown nonwoven fabric, or a SMS (spunbond-meltblown-spunbond) nonwoven fabric, on which water-repellent treatment may be applied as necessary.

As shown in FIGS. 4 and 5, two elastic yarns 31 extending in the longitudinal direction are bonded to each of the pair of side wall parts 3 and the elastic yarns 31 are extended in the expanded absorbent product 1 shown in FIG. 4. In the absorbent product 1, the elastic yarns 31 contract to stand up the side wall parts 3 toward the wearer on the right and left sides of the absorbent 2, to form standing gathers which come into contact with the vicinity of wearer's crotch in wearing.

The side wall parts 3 are made of water-repellent or liquid-impervious nonwoven fabric (i.e., spunbond nonwoven fabric, meltblown nonwoven fabric, or SMS nonwoven fabric), plastic film, or combinations of these materials. From the viewpoint of improving comfort of the absorbent product 1, it is preferable the side wall parts 3 have breathability. As the elastic yarns 31, polyurethane yarn, strip-like polyurethane film, yarn-like or strip-like natural rubber, or the like are used for example.

As shown in FIG. 5, the outer covering sheet 4 has a first sheet 41 and a second sheet 42 which is laminated on the first sheet 41 to be bonded with the first sheet 41 by the hot melt adhesive. In FIG. 5, a space is provided between the first sheet 41 and the second sheet 42 for convenience of illustration. The back sheet 23 of the absorbent 2 is bonded on the second sheet 42 of the outer covering sheet 4 by the hot melt adhesive or the like. The first sheet 41 and the second sheet 42 are water-repellent or liquid-impervious nonwoven fabrics in the present preferred embodiment. Though a water-repellent or liquid-impervious plastic film or a laminated sheet of plastic film and nonwoven fabric may be used as the first sheet 41 and the second sheet 42, it is preferable the first sheet 41 and the second sheet 42 are formed of nonwoven fabric from the view point of improving feel of the absorbent product 1.

As shown in FIGS. 1 to 3, the outer covering sheet 4 further has a waist elastic member 43 which is located along an edge of the waist opening 11, leg elastic members 44 which are located along edges of the pair of leg openings 12, respectively, a front elastic member 45 and a back elastic member 46 which are located on the front part 401 and the back part 403, respectively, along the horizontal direction (i.e., the width direction) between the waist elastic member 43 and the leg elastic members 44, and a first middle elastic member 47 and a second middle elastic member 48 which are located along the horizontal direction on the middle front part 4022 and the middle back part 4023 in the middle part 402 between the pair of leg openings 12.

As shown in FIG. 5, the leg elastic members 44 are bonded with the first sheet 41 and the second sheet 42 between the first sheet 41 and the second sheet 42, by using the hot melt adhesive or the like. The waist elastic member 43, the front elastic member 45 and the back elastic member 46, and the first middle elastic member 47 and the second middle elastic member 48 shown in FIGS. 1 to 3 are bonded with the first sheet 41 and the second sheet 42 between the first sheet 41 and the second sheet 42 shown in FIG. 5, by using the hot melt adhesive or the like, similarly to the leg elastic members 44.

As shown in FIG. 1, the extended waist elastic member 43 is bonded along the edge of the waist opening 11 around the almost whole waist opening 11. By contracting the waist elastic member 43, the first sheet 41 and the second sheet 42 (see FIG. 5) contract to form waist opening gathers. The extended leg elastic members 44 are bonded along the edges of the pair of leg openings 12, respectively, and by contracting the leg elastic members 44, the first sheet 41 and the second sheet 42 contract to form a pair of leg opening gathers.

The extended front elastic member 45 and the extended back elastic member 46 are bonded on the front part 401 and the back part 403 of the outer covering sheet 4, respectively. By contracting the front elastic member 45 and the back elastic member 46, the first sheet 41 and the second sheet 42 contract to form front gathers and back gathers. The extended first middle elastic member 47 and the extended second middle elastic member 48 shown in FIGS. 2 and 3 are bonded on the middle front part 4022 and the middle back part 4023 of the middle part 402, respectively. By contracting the first middle elastic member 47 and the second middle elastic member 48, the first sheet 41 and the second sheet 42 (see FIG. 5) contract to form middle gathers.

Since the middle gathers are provided in the absorbent product 1, fitting of the middle part 402 to the wearer can be improved and the appearance of the absorbent product 1 is enhanced. Also in a state where excrement such as urine is absorbed by the absorbent 2, since great expansion of the middle part 402 is suppressed by the middle gathers, it is possible to enhance the appearance of the absorbent product 1 and to surely prevent leak of the excrement from the absorbent product 1.

As discussed above, (a part of) the outer covering sheet 4 which is a part of the absorbent product 1 is an elastic sheet with elasticity in the vicinity of the waist opening 11, in the vicinities of the leg openings 12, the front part 401, the middle part 402, and the back part 403. In the present preferred embodiment, the waist elastic member 43, the leg elastic members 44, the front elastic member 45 and the back elastic member 46, and the first middle elastic member 47 and the second middle elastic member 48 are bonded with the first sheet 41 and the second sheet 42, respectively, in a state where they are preferably extended 1.1 to 5.0 times what they are.

As shown in FIGS. 2 and 4, both ends of the first middle elastic member 47 are apart from edges 121 of the pair of leg openings 12 in the outer covering sheet 4. A pair of non-contracted parts 49 are provided between the both ends of the first middle elastic member 47 and the edges 121 of the pair of leg openings 12 (the pair of non-contracted parts 49 are surrounded by double-dash lines in FIGS. 2 to 4). As shown in FIGS. 3 and 4, both ends of the second middle elastic member 48 are also apart from the edges 121 of the pair of leg openings 12, and a pair of non-contracted parts 49 are provided between the both ends of the second middle elastic member 48 and the edges 121 of the pair of leg openings 12.

As shown in FIGS. 2 to 4, the first middle elastic member 47 is continuous between the pair of non-contracted parts 49 in the middle front part 4022, and the second middle elastic member 48 is continuous between the pair of non-contracted parts 49 in the middle back part 4023, to form continuous middle gathers between each of the pairs of non-contracted parts 49.

In a state where the first sheet 41 and the second sheet 42 of the outer covering sheet 4 are expanded in the absorbent product 1 (see FIG. 4), it is preferable a length in the horizontal direction of the first middle elastic member 47 is equal to or larger than 40% and equal to or smaller than 80% of a width in the horizontal direction of the middle front part 4022 at a position where the first middle elastic member 47 is provided, and more preferably, the length is equal to or larger than 50% and equal to or smaller than 70% of the width. In this case, the width in the horizontal direction of the middle front part 4022 at the position where the first middle elastic member 47 is provided, is an average width in the horizontal direction of the middle front part 4022 at the portion, and the width is that in the horizontal direction of the middle front part 4022 in the vicinity of a position where a central first middle elastic yarn 471, out of three first middle elastic yarns 471 of the first middle elastic member 47, is provided (the three first middle elastic yarns 471 are discussed later). Also, it is preferable a length in the horizontal direction of the second middle elastic member 48 is equal to or larger than 40% and equal to or smaller than 80% of an average width in the horizontal direction of the middle back part 4023 at a position where the second middle elastic member 48 is provided, and more preferably, the length is equal to or larger than 50% and equal to or smaller than 70% of the width.

In other words, in the state where the first sheet 41 and the second sheet 42 of the outer covering sheet 4 are expanded in the absorbent product 1, a total width in the horizontal direction of the pair of non-contracted parts 49 in the middle front part 4022 is preferably equal to or larger than 20% and equal to or smaller than 60% of an average width in the horizontal direction of the middle front part 4022 at a position where the pair of non-contracted parts 49 are provided (the average width is equal to that in the horizontal direction at the position where the first middle elastic member 47 is provided, which is discussed above), and more preferably, the total width is equal to or larger than 30% and equal to or smaller than 50% of the average width. Also, a total width in the horizontal direction of the pair of non-contracted parts 49 in the middle back part 4023 is preferably equal to or larger than 20% and equal to or smaller than 60% of an average width in the horizontal direction of the middle back part 4023 at a position where the pair of non-contracted parts 49 are provided (more preferably, equal to or larger than 30% and equal to or smaller than 50%).

In the middle front part 4022, the leg elastic members 44 are not provided in the pair of non-contracted parts 49 as shown in FIG. 2. That is, the leg elastic members 44 are divided into upper portions and a lower portion by the pair of non-contracted parts 49, and portions above the non-contracted parts 49 (i.e., portions on the side of the front part 401) of the leg elastic members 44 are located between the non-contracted parts 49 and the vicinities of lower ends of side end portions of the front part 401, along the edges 121 of the pair of leg openings 12, respectively. A portion below the non-contracted parts 49 (i.e., a portion opposite to the front part 401) of the leg elastic members 44 is located from one non-contracted part 49 to the vicinity of the folded part 4021 along one leg opening 12 and located in the vicinity of the folded part 4021 along the horizontal direction and further, located from the vicinity of the folded part 4021 to the other non-contracted part 49 along the other leg opening 12.

In the middle back part 4023, the leg elastic members 44 are not provided in the pair of non-contracted parts 49 as shown in FIG. 3, similarly to the middle front part 4022 (see FIG. 2), and the leg elastic members 44 are divided into upper portions and a lower portion by the pair of non-contracted parts 49. Portions above the non-contracted parts 49 of the leg elastic members 44 are located between the non-contracted parts 49 and the vicinities of lower ends of side end portions of the back part 403, along the edges 121 of the pair of leg openings 12, respectively. A portion below the non-contracted parts 49 of the leg elastic members 44 is located from one non-contracted part 49 to the vicinity of the folded part 4021 along one leg opening 12 and located in the vicinity of the folded part 4021 along the horizontal direction and further, located from the vicinity of the folded part 4021 to the other non-contracted part 49 along the other leg opening 12.

Therefore, the right and left ends of the front part 401 and the back part 403 of the outer covering sheet 4 shown in FIGS. 2 and 3 are bonded with each other and thereby, the leg elastic members 44 are intermittently (discontinuously) positioned around the pair of leg openings 12 in a non-circular shape.

As shown in FIGS. 1 to 4, the waist elastic member 43, the front elastic member 45 and the back elastic member 46, and the first middle elastic member 47 and the second middle elastic member 48 are elastic yarn groups each including elastic yarns which are a plurality of elastic elements. In the absorbent product 1, these elastic yarn groups are collectively called as "the waist elastic member 43", "the front elastic member 45 and the back elastic member 46", and "the first middle elastic member 47 and the second middle elastic member 48", respectively.

A plurality of elastic yarns included in the waist elastic member 43 are separately provided in the front part 401 and the back part 403 of the outer covering sheet 4, as shown in FIG. 4. The right and left ends of the front part 401 and the back part 403 are bonded with each other, and the plurality of elastic yarns included in the waist elastic member 43 are thereby positioned along the edge of the waist opening 11 (see FIG. 1) of the absorbent product 1 around the almost whole waist opening 11. The right and left ends of the front part 401 and the back part 403 of the outer covering sheet 4 are bonded with each other, and a plurality of elastic yarns included in the front elastic member 45 and a plurality of elastic yarns included in the back elastic member 46 are thereby positioned around the almost whole waist part (i.e., the front part 401 and the back part 403) between the waist opening 11 and the pair of leg openings 12.

In the middle front part 4022 (and the front part 401) of the outer covering sheet 4, three elastic yarns 441 included in the leg elastic members 44 are arranged in the vicinity of each leg opening 12 in nearly parallel with the edge 121 of the leg opening 12, as shown in FIG. 2. In the middle back part 4023 (and the back part 403), three elastic yarns 442 included in the leg elastic members 44 are arranged in the vicinity of each leg opening 12 in nearly parallel with the edge 121 of the leg opening 12, as shown in FIG. 3. In the following description, the elastic yarns 441, 442 are referred to as "front part leg elastic yarns 441" and "back part leg elastic yarns 442", respectively.

As shown in FIG. 2, the first middle elastic member 47 has three first middle elastic yarns 471. Each first middle elastic yarn 471 is continuous between the pair of non-contracted parts 49 in the middle front part 4022 and the first middle elastic yarns 471 are arranged in nearly parallel with the horizontal direction. As shown in FIG. 3, the second middle elastic member 48 has three second middle elastic yarns 481 similarly to the first middle elastic member 47, and each second middle elastic yarn 481 is continuous between the pair of non-contracted parts 49 in the middle back part 4023 and the second middle elastic yarns 481 are arranged in nearly parallel with the horizontal direction.

Examples of the plurality of elastic yarns included in each of the waist elastic member 43, the leg elastic members 44, the front elastic member 45 and the back elastic member 46, and the first middle elastic member 47 and the second middle elastic member 48 shown in FIG. 4, are polyurethane yarn, strip-like polyurethane film, yarn-like or strip-like natural rubber, or the like. In the present preferred embodiment, a plurality of polyurethane yarns which are yarn-like members with a fineness of 300 to 2000 decitex (dtex) are bonded with the first sheet 41 and the second sheet 42 (see FIG. 5) by rubber hot melt adhesive. Bonding methods such as ultrasonic compression bonding and thermo compression bonding can be used for adhering the elastic yarns included in each elastic member with the first sheet 41 and the second sheet 42. From the view point of simplification of the manufacturing or the like, however, bonding with the hot melt adhesive is preferable.

Figure 6A:
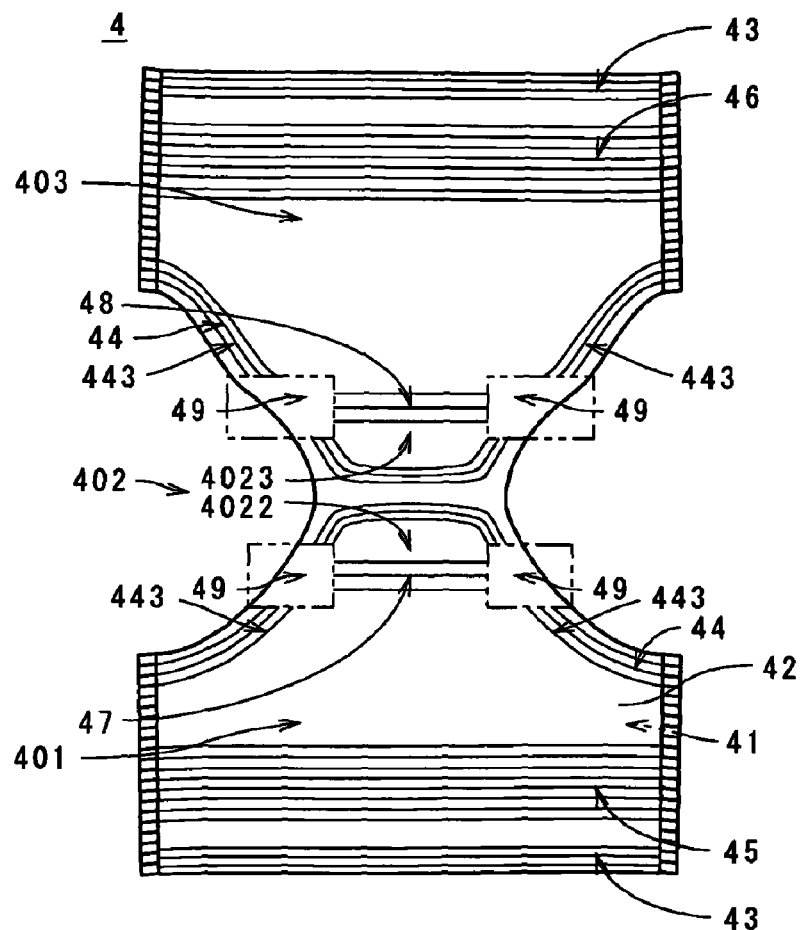
FIG. 6A is a plan view of an outer covering sheet in a state where the outer covering sheet is spread.

FIG. 6A is a plan view of the outer covering sheet 4 as viewed from the wearer's side in a state where the outer covering sheet 4 is spread (i.e., a state where the right and left ends of the front part 401 and the back part 403 are not bonded with each other). In the state where the first sheet 41 and the second sheet 42 of the outer covering sheet 4 are expanded as shown in FIG. 6A, the waist elastic member 43, the leg elastic members 44, the front elastic member 45 and the back elastic member 46, and the first middle elastic member 47 and the second middle elastic member 48 are respectively extended. In FIG. 6A, the waist elastic member 43, the leg elastic members 44, the front elastic member 45 and the back elastic member 46, and the first middle elastic member 47 and the second middle elastic member 48 are shown by thin solid lines for convenience of illustration.

As shown in FIG. 6A, the pair of leg elastic members 44 have a pair of inclined parts 443 each of which is inclined relatively to both of the longitudinal direction of the outer covering sheet 4 (i.e., the longitudinal direction is the vertical direction in FIG. 6A and corresponds to the longitudinal direction of the absorbent product 1) and the width direction (i.e., the horizontal direction) perpendicular to the longitudinal direction in each of the middle front part 4022 and the middle back part 4023. In the outer covering sheet 4, it is preferable that an angle relative to the longitudinal direction of the inclined parts 443 in the vicinity of the non-contracted parts 49 in the middle front part 4022, is about 20 to 45 degrees, and it is preferable that an angle relative to the longitudinal direction of the inclined parts 443 in the vicinity of the non-contracted parts 49 in the middle back part 4023, is about 20 to 50 degrees.

The horizontal direction, i.e., a direction where the first middle elastic member 47 and the second middle elastic member 48 are positioned, is referred to as a "first direction" and a direction where one inclined part 443 of the leg elastic members 44 is positioned, is referred to as a "second direction". The first middle elastic member 47 and the second middle elastic member 48 shown in FIGS. 2 and 3 have a plurality of first middle elastic yarns 471 and a plurality of second middle elastic yarns 481 along the first direction, respectively, and the above inclined part 443 (see FIG. 6A) has a plurality of front part leg elastic yarns 441 or a plurality of back part leg elastic yarns 442 along the second direction tilted relatively to the first direction.

As shown in FIG. 6A, the non-contracted part 49 is provided on each of the inclined parts 443 on right and left sides of the first middle elastic member 47 and the second middle elastic member 48 in the outer covering sheet 4. The pair of non-contracted parts 49 are formed by cutting extended elastic yarns which are bonded with the first sheet 41 and the second sheet 42 through areas to be the non-contracted parts 49, at a plurality of positions in the areas, together with the first sheet 41 and the second sheet 42, to lose elasticity of portions in the pair of non-contracted parts 49 (i.e., the extended elastic yarns are the first middle elastic yarns 471 and the front part leg elastic yarns 441 shown in FIG. 2 or the second middle elastic yarns 481 and the back part leg elastic yarns 442 shown in FIG. 3).

Figure 6B:
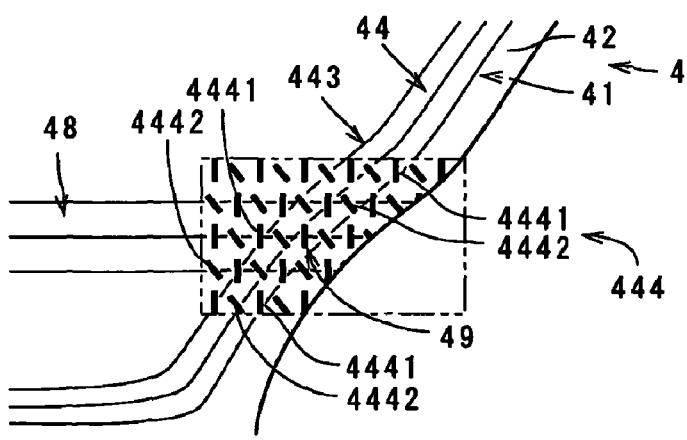
FIG. 6B is an enlarged plan view showing the vicinity of a non-contracted part.

FIG. 6B is an enlarged plan view showing the vicinity of one non-contracted part 49 in the outer covering sheet 4 shown in FIG. 6A. As shown in FIG. 6B, the second sheet 42 has a plurality of cutting lines 444 which are formed by cutting the above extended elastic yarns in each non-contracted part 49. The first sheet 41 also has a plurality of cutting lines which overlap with the plurality of cutting lines 444 formed in the second sheet 42. In other words, the above extended elastic yarns are cut at positions of the plurality of cutting lines 444 and an area in which the plurality of cutting lines 444 exist becomes the non-contracted part 49 in the outer covering sheet 4. Pieces of cut elastic yarns contract between the first sheet 41 and the second sheet 42 without contracting the first sheet 41 and the second sheet 42.

The plurality of cutting lines 444 include two types of cutting lines 4441, 4442 whose directions are different from each other. A plurality of cutting lines 4441 and a plurality of cutting lines 4442 are tilted relatively to both of the horizontal direction of the outer covering sheet 4 where the first middle elastic member 47 and the second middle elastic member 48 (see FIG. 6A) are positioned and the direction where the inclined part 443 of the leg elastic members 44 in each non-contracted part 49 is positioned (i.e., both of the above first direction and the second direction). In the following description, the cutting lines 4441 along the longitudinal direction of the outer covering sheet 4 are referred to as "first cutting lines 4441" and the cutting lines 4442 along a direction tilted relatively to the first cutting lines 4441 are referred to as "second cutting lines 4442". The plurality of first cutting lines 4441 and the plurality of second cutting lines 4442 are almost uniformly distributed and arranged in each of the non-contracted parts 49 in the outer covering sheet 4 shown in FIG. 6A.

In the outer covering sheet 4, it is preferable the first cutting lines 4441 (see FIG. 6B) in each non-contracted part 49 are tilted relatively to the first direction where the first middle elastic member 47 and the second middle elastic member 48 (before cut) in the non-contracted part 49 are positioned, at an angle which is equal to or larger than 45 degrees and equal to or smaller than 135 degrees, and it is more preferable the first cutting lines 4441 are tilted relatively to the first direction, at an angle which is equal to or larger than 80 degrees and equal to or smaller than 100 degrees. In the present preferred embodiment, an angle formed between the first cutting lines 4441 in each non-contracted part 49 and the first middle elastic member 47 and an angle formed between the first cutting lines 4441 and the second middle elastic member 48, are about 90 degrees as described above.

It is preferable the second cutting lines 4442 (see FIG. 6B) in each non-contracted part 49 are tilted relatively to the second direction where the inclined part 443 of the leg elastic members 44 (before cut) in the non-contracted part 49 is positioned, at an angle which is equal to or larger than 45 degrees and equal to or smaller than 135 degrees, and it is more preferable that the second cutting lines 4442 are tilted relatively to the second direction, at an angle which is equal to or larger than 80 degrees and equal to or smaller than 100 degrees. In the present preferred embodiment, an angle formed between the second cutting lines 4442 in each non-contracted part 49 and the inclined part 443 is about 90 degrees.

Figure 7:
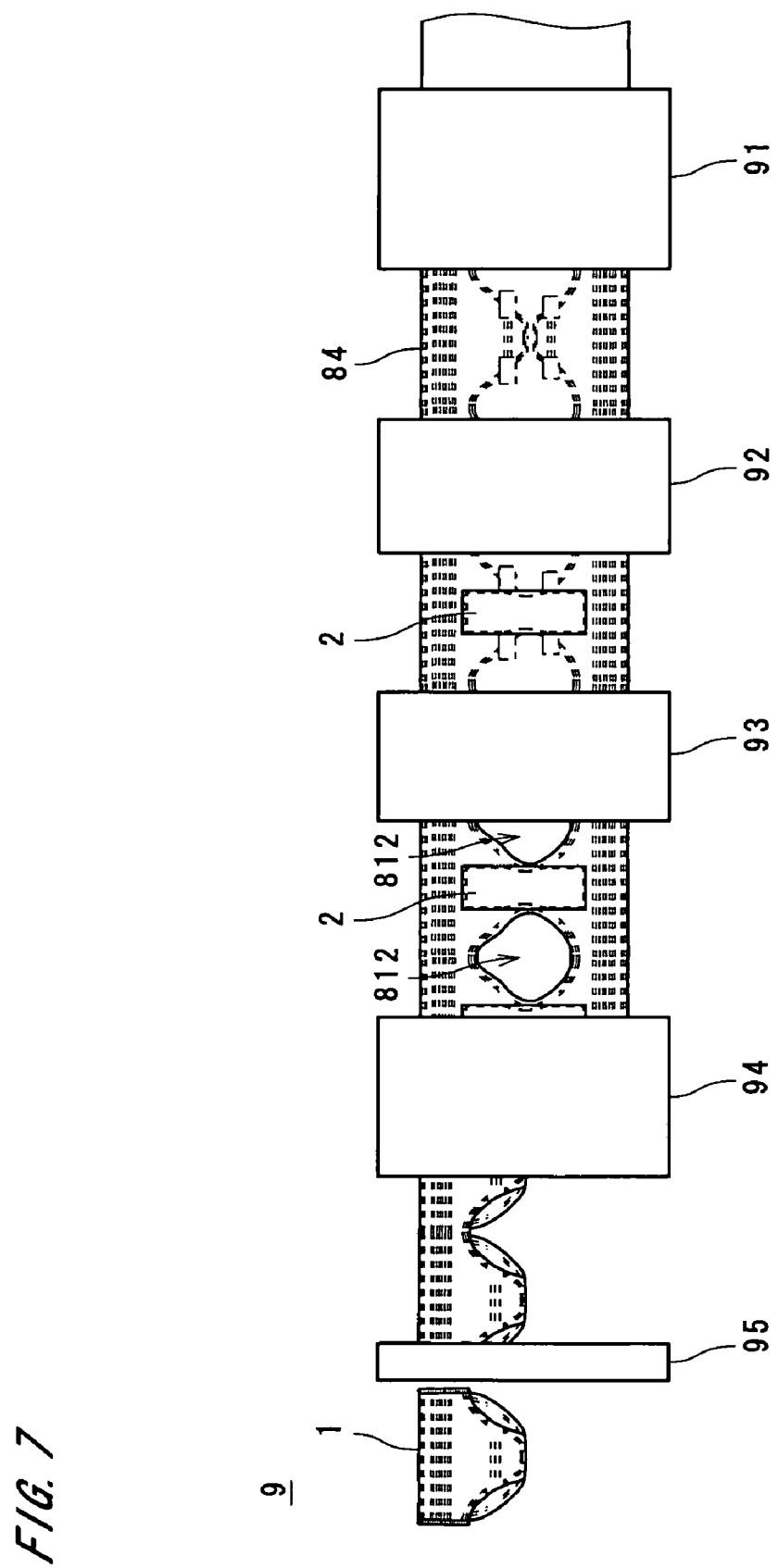
FIG. 7 is a view showing a construction of a manufacturing apparatus of the absorbent product.

Next discussion will be made on manufacturing of the absorbent product 1. FIG. 7 is a view showing a construction of a manufacturing apparatus 9 of the absorbent product 1. As shown in FIG. 7, the manufacturing apparatus 9 has an outer covering sheet forming part 91 for forming an outer covering sheet member 84 which is to be the outer covering sheet 4 (see FIG. 6A) in the absorbent product 1, an absorbent bonding part 92 for bonding the absorbent 2, which is separately formed, on the outer covering sheet member 84, an opening forming part 93 for forming a hole 812 in the outer covering sheet member 84, which are to be the leg openings 12 (see FIG. 1) in the absorbent product 1, a folding part 94 for folding the outer covering sheet member 84 into two to form the outer covering sheet member 84 in a shape of underpants, and a cutting part 95 for cutting the outer covering sheet member 84 to obtain the absorbent product 1.

In the manufacturing apparatus 9, manufacturing of the absorbent product 1 is performed while the outer covering sheet member 84 is transferred from the outer covering sheet forming part 91 to the cutting part 95 (i.e., from the right side to the left side in FIG. 7). The outer covering sheet member 84 is a continuous body of the outer covering sheets 4 in the width direction, and a transfer direction of the outer covering sheet member 84 corresponds to the width direction (horizontal direction) of the outer covering sheet 4 and the absorbent product 1. That is, in the manufacturing apparatus 9, the direction where the first middle elastic member 47 and the second middle elastic member 48 are positioned in the outer covering sheet 4 shown in FIG. 6A, is parallel to the transfer direction of the outer covering sheet member 84, and the direction where each inclined part 443 of the leg elastic members 44 is positioned, is tilted relatively to the transfer direction of the outer covering sheet member 84.

Figure 8A:
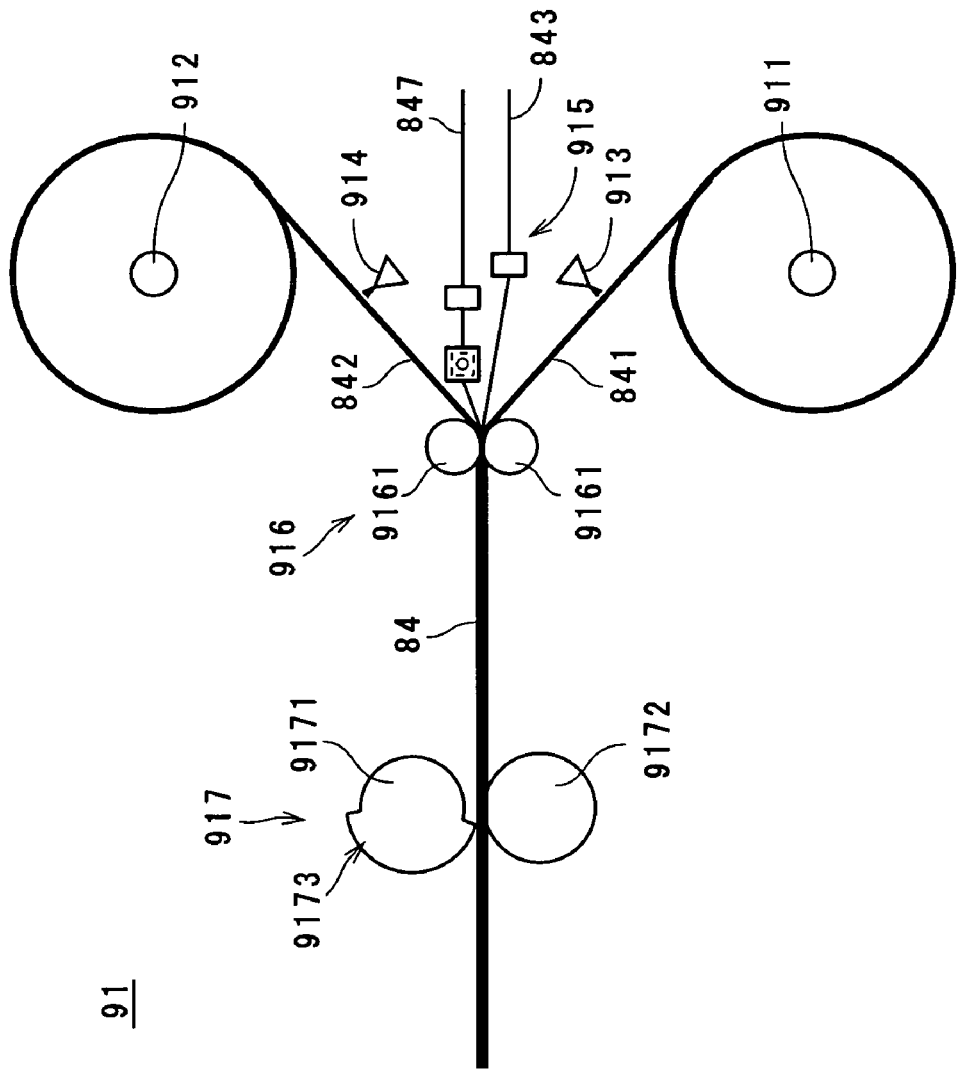
FIG. 8A is a side view of an outer covering sheet forming part.
Figure 8B:
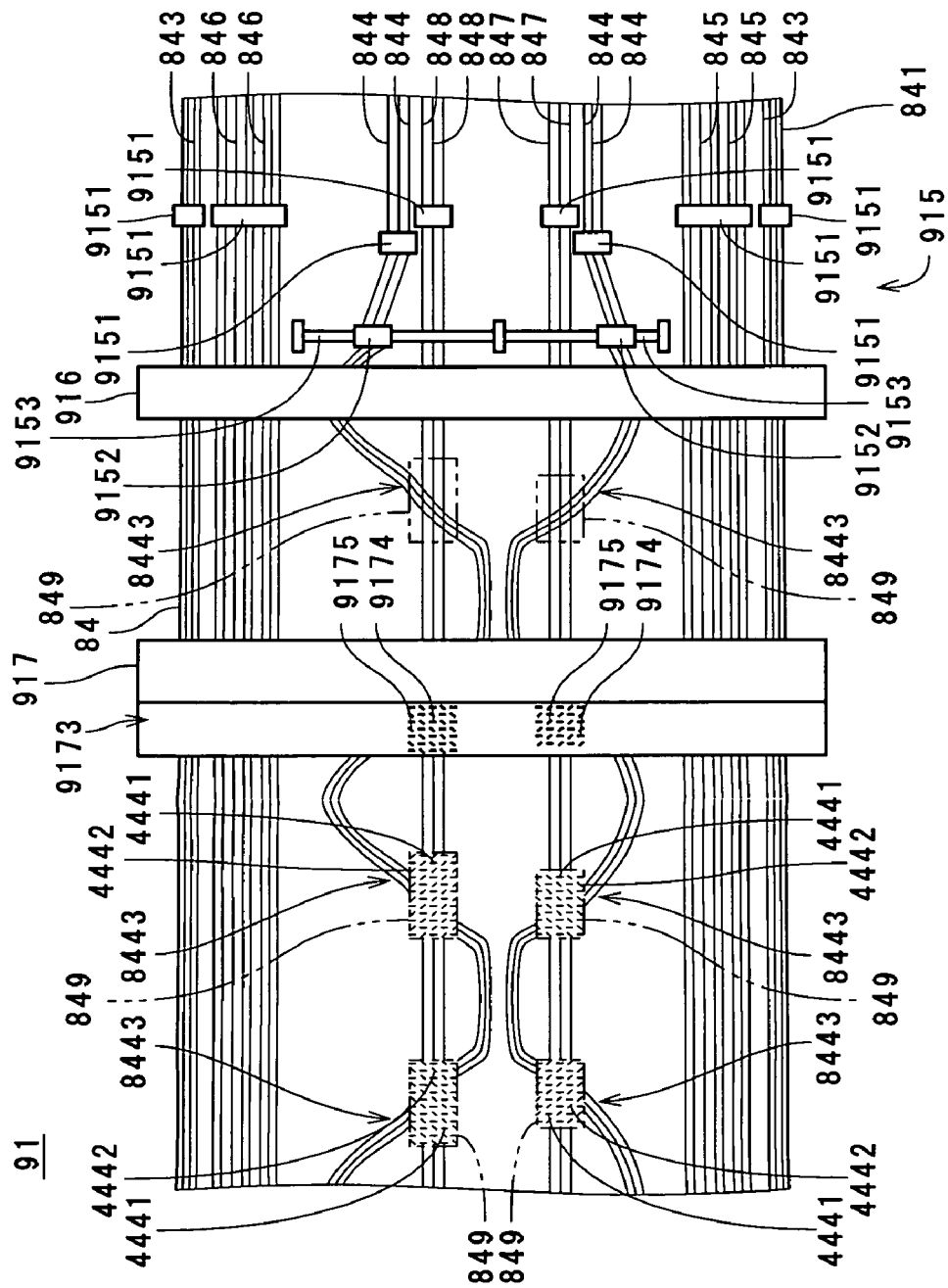
FIG. 8B is a plan view of the outer covering sheet forming part.

FIG. 8A is a side view of the outer covering sheet forming part 91 and FIG. 8B is a plan view of the outer covering sheet forming part 91. As shown in FIG. 8A, the outer covering sheet forming part 91 has roll fitted parts 911, 912 on which rolls of a first sheet member 841 and a second sheet member 842, which are to be the first sheets 41 and the second sheets 42 (see FIG. 5) in the outer covering sheets 4, are fitted, respectively, adhesive applying parts 913, 914 for applying the hot melt adhesive onto the first sheet member 841 and the second sheet member 842, and an elastic member feeding part 915 for feeding elastic members between the first sheet member 841 and the second sheet member 842, as shown in FIGS. 8A and 8B. In FIG. 8B, the roll fitted parts 911, 912, the adhesive applying parts 913, 914, and the second sheet member 842 above the elastic member feeding part 915 are omitted for convenience of illustration. Elastic yarns 843 to 848 are shown by thin solid lines in FIG. 8B and elastic yarns 843, 847 are only shown in FIG. 8A.

As shown in FIG. 8B, the elastic member feeding part 915 has fixed guides 9151 for guiding the elastic yarns 843, 844, 845, 846, 847, 848 which are elastic members to be the waist elastic member 43, the leg elastic members 44, the front elastic member 45, the back elastic member 46, the first middle elastic member 47 and the second middle elastic member 48 (see FIG. 6A) in the outer covering sheet 4 and two moving guides 9152 for changing guiding positions of the elastic yarns 844 on downstream sides of the fixed guides 9151. The two moving guides 9152 are individually moved by a guide moving mechanism, along a guide rod 9153 which extends in a direction perpendicular to the transfer direction of the outer covering sheet member 84 (i.e., the direction is a vertical direction in FIG. 8B). One moving guide 9152 located on a lower side of FIG. 8B guides elastic yarns 844 which are to be the three front part leg elastic yarns 441 (see FIG. 2) included in the leg elastic members 44, and the other moving guide 9152 guides elastic yarns 844 which are to be the three back part leg elastic yarns 442 (see FIG. 3) included in the leg elastic members 44.

In the elastic member feeding part 915, extended elastic yarns 843 to 848 are fed in the transfer direction of the outer covering sheet member 84 by a not-shown feeding mechanism and guided in parallel with the transfer direction by the fixed guides 9151, and then the elastic yarns 843 to 848 are fed between the first sheet member 841 and the second sheet member 842 (see FIG. 8A). In this time, the moving guides 9152 move along the guide rod 9153 and thereby, the elastic yarns 844 are guided in a direction tilted relatively to both of the transfer direction of the outer covering sheet member 84 and the direction perpendicular to the transfer direction.

As shown in FIGS. 8A and 8B, the outer covering sheet forming part 91 further has a pressing part 916 which sandwiches and presses the first sheet member 841 and the second sheet member 842 and an elastic member cutting part 917 for partially cutting elastic members. As shown in FIG. 8A, the pressing part 916 has two nip rolls 9161 each of which rotates around a rotation axis extending in a direction which is perpendicular to the transfer direction of the outer covering sheet member 84 and parallel to the outer covering sheet member 84 (i.e., the direction is the vertical direction in FIG. 8B), on the upper side and the lower side of the outer covering sheet member 84.

The elastic member cutting part 917 has a rotating blade 9171 and an anvil roll 9172 each of which rotates around a rotation axis extending in the direction which is perpendicular to the transfer direction of the outer covering sheet member 84 and parallel to the outer covering sheet member 84 (i.e., the direction is the vertical direction in FIG. 8B), on the upper side and the lower side of the outer covering sheet member 84. The rotating blade 9171 rotates clockwise in FIG. 8A and the anvil roll 9172 rotates counterclockwise in FIG. 8A.

A convex part 9173 extending in parallel with the rotation axis is formed on the rotating blade 9171. An outer surface of the convex part 9173 shown in FIGS. 8A and 8B is provided with a plurality of first cutting blades 9174 and a plurality of second cutting blades 9175 which correspond to the plurality of first cutting lines 4441 and the plurality of second cutting lines 4442 (see FIG. 6B), respectively, included in the four non-contracted parts 49 in the outer covering sheet 4 (i.e., the pair of non-contracted parts 49 in the middle front part 4022 and the pair of non-contracted parts 49 in the middle back part 4023) (FIG. 8B shows a plurality of first cutting blades 9174 and a plurality of second cutting blades 9175 which correspond to two non-contracted parts 49). In the outer surface of the convex part 9173, the plurality of first cutting blades 9174 and the plurality of second cutting blades 9175 are almost uniformly distributed in four areas where the first cutting blades 9174 and the second cutting blades 9175 are provided (i.e., the four areas are areas corresponding to the four non-contracted parts 49).

Figure 9:
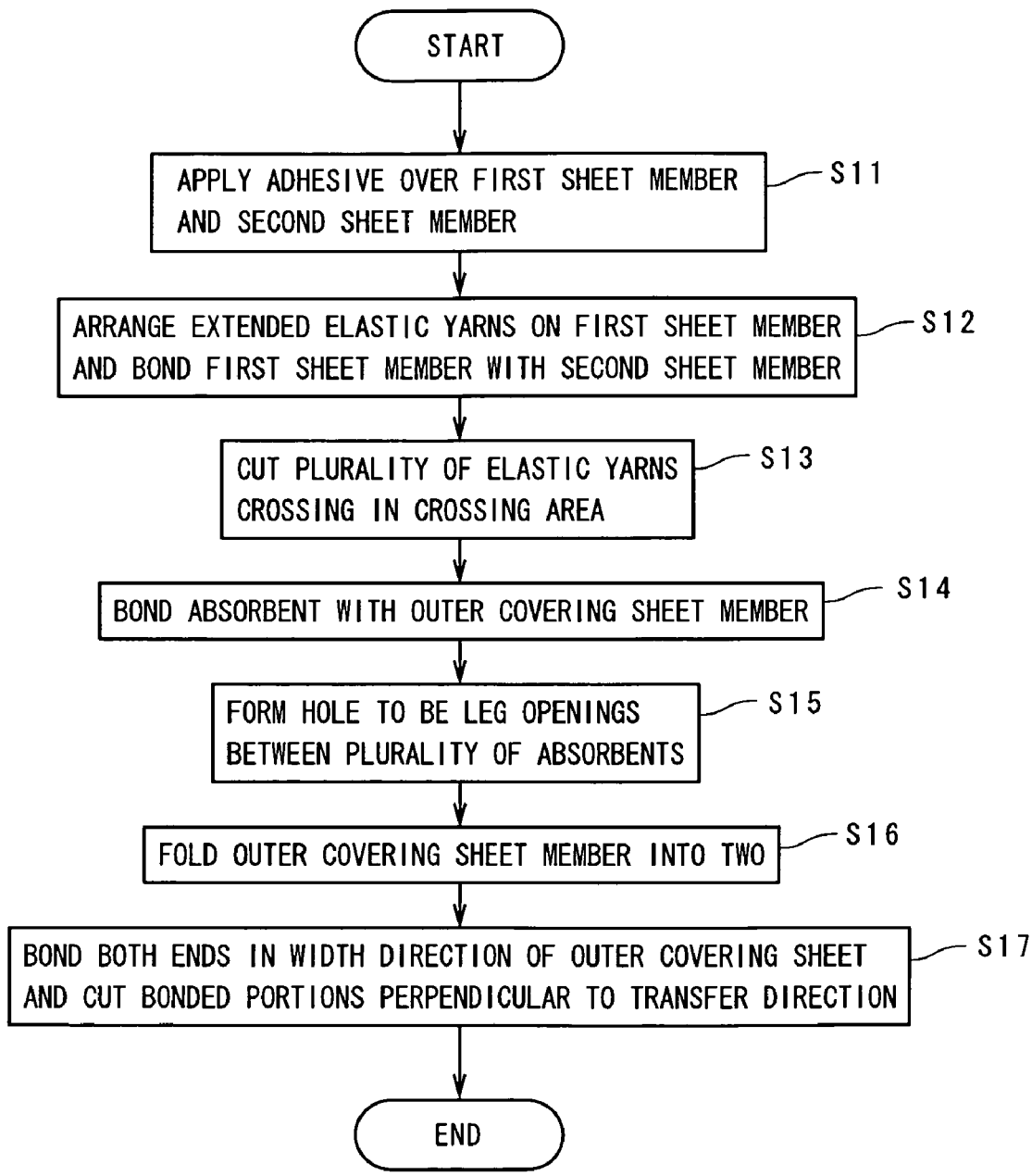
FIG. 9 is a flowchart showing a manufacturing flow of the absorbent product.

FIG. 9 is a flowchart showing a manufacturing flow of the absorbent product 1. In manufacturing the absorbent product 1 by the manufacturing apparatus 9 shown in FIG. 7, first, the first sheet member 841 and the second sheet member 842 are led out from the rolls of the first sheet member 841 and the second sheet member 842 which are fitted on the roll fitted parts 911, 912 shown in FIG. 8A in the outer covering sheet forming part 91, and the adhesive applying parts 913, 914 apply the hot melt adhesive over one surfaces of the first sheet member 841 and the second sheet member 842, with use of a curtain spray or the like (Step S11).

Subsequently, the elastic member feeding part 915 shown in FIG. 8B feeds the extended elastic yarns 843 to 848 between the first sheet member 841 and the second sheet member 842 which are transferred in the transfer direction, as shown in FIG. 8A. In this time, the hot melt adhesive is applied over the entire lengths of the elastic yarns 843, 845 to 848 and then, the elastic yarns 843, 845 to 848 are fed between the first sheet member 841 and the second sheet member 842. The moving guides 9152 in the elastic member feeding part 915 shown in FIG. 8B move as necessary and thereby, a part of the extended elastic yarns 844 are arranged on the first sheet member 841 as inclined parts 8443 which are tilted relatively to both of the transfer direction and the direction perpendicular to the transfer direction. The inclined parts 8443 of the elastic yarns 844 become the inclined parts 443 in the leg elastic members 844 shown in FIG. 6A.

As shown in FIG. 8A, the first sheet member 841 and the second sheet member 842 are sandwiched between the two nip rolls 9161 of the pressing part 916, and thereby, the second sheet member 842 is laminated on the first sheet member 841 with interposing the extended elastic yarns 843 to 848 (see FIG. 8B) and the first sheet member 841 and the second sheet member 842 are bonded with each other. The elastic yarns 843 to 848 are also bonded with the first sheet member 841 and the second sheet member 842 (Step S12).

As shown in FIG. 8B, extended three elastic yarns 847, 848 which are arranged on the first sheet member 841 along the transfer direction of the first sheet member 841 (i.e., the three elastic yarns 847, 848 are elastic yarns to be the first middle elastic member 47 and the second middle elastic member 48) cross extended three elastic yarns 844 in areas 849 surrounded by double-dashed lines in FIG. 8B, respectively, the three elastic yarns 844 being arranged on the first sheet member 841 along the direction tilted relatively to the transfer direction of the first sheet member 841 (i.e., the three elastic yarns 844 are elastic yarns to be the leg elastic members 44). In the following description, the areas 849 in the vicinities of a plurality of intersection points of elastic yarns, the areas 849 including the plurality of intersection points, are referred to as "crossing areas 849".

Next, the outer covering sheet member 84 is sandwiched between the rotating blade 9171 and the anvil roll 9172 of the elastic member cutting part 917 shown in FIG. 8A, and the elastic yarns 844 and the elastic yarns 847 crossing in each crossing area 849 or the elastic yarns 844 and the elastic yarns 848 crossing in each crossing area 849 are cut by the plurality of first cutting blades 9174 and the plurality of second cutting blades 9175 of the rotating blade 9171 shown in FIG. 8B, together with the first sheet member 841 and the second sheet member 842 (see FIG. 8A), to form the plurality of first cutting lines 4441 and the plurality of second cutting lines 4442 in each of the crossing areas 849 (Step S13). The plurality of first cutting lines 4441 formed by the plurality of first cutting blades 9174 and the plurality of second cutting lines 4442 formed by the plurality of second cutting blades 9175 are almost uniformly distributed in the crossing area 849.

In a state where the first cutting blades 9174 and the second cutting blades 9175 face the crossing area 849, the first cutting blades 9174 are preferably tilted relatively to the first direction where the elastic yarns 847, 848 (before cut) are arranged in the crossing area 849, at an angle which is equal to or larger than 45 degrees and equal to or smaller than 135 degrees (more preferably, equal to or larger than 80 degrees and equal to or smaller than 100 degrees). An angle formed between the first cutting blades 9174 and each of the elastic yarns 847, 848 is about 90 degrees in the present preferred embodiment. The second cutting blades 9175 are preferably tilted relatively to the second direction where the inclined part 8443 of the elastic yarns 844 (before cut) is positioned in the crossing area 849, at an angle which is equal to or larger than 45 degrees and equal to or smaller than 135 degrees (more preferably, equal to or larger than 80 degrees and equal to or smaller than 100 degrees). An angle formed between the second cutting blades 9175 and the inclined part 8443 of the elastic yarns 844 is about 90 degrees in the present preferred embodiment.

In the outer covering sheet member 84, portions to which the elastic yarns 843 to 848 are bonded become contracted parts. Out of the contracted parts, the inclined parts 8443 of the elastic yarns 844 and the crossing areas 849 in which the elastic yarns 847, 848 are partially cut (i.e., areas in which the plurality of first cutting lines 4441 and the plurality of second cutting lines 4442 exist) become non-contracted parts. The non-contracted parts are the non-contracted parts 49 in the outer covering sheet 4 shown in FIG. 6A. The outer covering sheet member 84 is a continuous body of portions to be the outer covering sheets 4 in the absorbent products 1, as discussed above. Looking at a portion corresponding to one outer covering sheet 4, the portion is an elastic sheet having contracted parts and non-contracted parts.

After formation of the outer covering sheet member 84, the outer covering sheet member 84 is transferred to the absorbent bonding part 92 shown in FIG. 7. In the absorbent bonding part 92, the hot melt adhesive is applied onto the second sheet member 842 (see FIG. 8A) of the outer covering sheet member 84, and the absorbent 2 which is separately formed is placed on the hot melt adhesive applied onto the second sheet member 842 to be bonded with the outer covering sheet member 84 (Step S14). Subsequently, each of portions between a plurality of absorbents 2 is partially removed in the opening forming part 93, to form an approximately circular hole 812 which is to be the leg openings 12 (see FIG. 1) (Step S15).

In the folding part 94, the outer covering sheet member 84 is folded into two, in a fold line parallel to the transfer direction in the vicinity of the central portion in the direction perpendicular to the transfer direction of the outer covering sheet member 84 (Step S16). In the cutting part 95, the both ends in the width direction of the front part 401 and the back part 403 in the outer covering sheet 4 (see FIG. 6A) are bonded by heat sealing or the like and the heat-sealed portions are cut perpendicular to the transfer direction, to form the absorbent product 1 (Step S17).

As discussed above, in the outer covering sheet 4 of the absorbent product 1, (the elastic yarns 844 to be) the leg elastic members 44 and (the elastic yarns 847 to be) the first middle elastic member 47 are cut in the crossing areas of the leg elastic members 44 and the first middle elastic member 47, and (the elastic yarns 844 to be) the leg elastic members 44 and (the elastic yarns 848 to be) the second middle elastic member 48 are cut in the crossing areas of the leg elastic members 44 and the second middle elastic member 48, and the above crossing areas become the non-contracted parts 49, to thereby prevent the outer covering sheet 4 from being excessively contracted to become rigid in the crossing areas of the elastic members. The non-contracted parts 49 are formed in the outer covering sheet 4 by cutting the elastic members in the crossing areas as discussed above, to improve flexibility of the absorbent product 1. As a result, it is possible to provide the wearer with comfortable feeling in wearing the absorbent product 1.

Flexibility of portions in the vicinities of the leg openings 12 in the outer covering sheet 4 can be improved by providing the non-contracted parts 49 in the vicinities of the leg openings 12 in the absorbent product 1. As a result, it is possible to prevent the portions in the vicinities of the leg openings 12 in the absorbent product 1 from fitting too tightly to the wearer (i.e., prevent the legs of the wearer from being strongly compressed in the absorbent product 1) and to provide the wearer with comfortable feeling in wearing the absorbent product 1 while preventing leak of excrement. Further, the legs of the wearer can be smoothly inserted into the leg openings 12 in wearing the absorbent product 1, and the wearer can easily wear the absorbent product 1.

Normally, there are many cases that a wearer of a pants-type disposal diaper moves in the state of wearing the disposal diaper, as compared with a wearer of an open-type disposal diaper (i.e., such a type of disposal diaper that a portion located on a stomach side of the wearer and a portion located on a back side are fastened around waistline of the wearer by using a fastening tape or the like in wearing the disposal diaper). If the contraction force of an elastic member in the pants-type disposal diaper is large, there is a possibility that the elastic member is tightly fitted to wearer's skin (especially, skin in the vicinity of wearer's crotch) by movement of the wearer. In the absorbent product 1, since the non-contracted parts 49 are provided in the vicinities of the leg openings 12 in the outer covering sheet 4 as discussed above and it is possible to prevent tight fitting of the elastic member to wearer's skin, the above structure of the absorbent product 1 is especially suitable for a pants-type disposal diaper.

In manufacturing of the absorbent product 1, the elastic yarns 847, 848 to be the first middle elastic member 47 and the second middle elastic member 48 in the outer covering sheet 4 are cut by the first cutting blades 9174 which are tilted relatively to the direction where the elastic yarns 847, 848 are arranged, and each inclined part 8443 of the elastic yarns 844 to be the leg elastic members 44 are cut by the second cutting blades 9175 which are tilted relatively to the direction where the inclined part 8443 of the elastic yarns 844 is positioned. Thus, it is possible to prevent the elastic yarns 844, 847, 848 from being positioned in small clearances between the plurality of cutting blades in the rotating blade 9171 and to reliably cut the elastic yarns 844, 847, 848. With this operation, it is possible to prevent decrease of flexibility of the outer covering sheet 4 in the crossing areas of these elastic yarns.

Since the plurality of cutting blades including the first cutting blades 9174 and the second cutting blades 9175 simultaneously cut elastic yarns crossing in both of the crossing area 849 of the elastic yarns 847 and the elastic yarns 844 and the crossing area 849 of the elastic yarns 848 and the elastic yarns 844, and the crossing areas 849 become the non-contracted parts 49, it is possible to easily form the outer covering sheet 4 which is an elastic sheet with high flexibility. In the above-discussed method of manufacturing the absorbent product 1, the elastic yarns crossing in the crossing areas of the elastic members can be simultaneously and reliably cut and therefore, the method is especially suitable for manufacturing of the outer covering sheet 4 in which each of the crossing elastic members has a plurality of elastic yarns (i.e., the outer covering sheet 4 having many elastic yarns which should be cut).

In the outer covering sheet 4 formed by the above method, since elastic members are appropriately positioned in the front part 401, the middle part 402 and the back part 403 with preventing cross of elastic members, it is possible to maintain elasticity in a required portion and improve flexibility of the outer covering sheet 4. By manufacturing the absorbent product 1 with use of the outer covering sheet 4 (i.e., by making the outer covering sheet 4 included in a part of the absorbent product 1), it is possible to easily manufacture the absorbent product 1 where elasticity in a required portion is maintained and flexibility is improved.

In manufacturing of the above absorbent product 1, the plurality of first cutting blades 9174 are arranged in the rotating blade 9171 of the elastic member cutting part 917 so that the first cutting blades 9174 are tilted relatively to the first direction where the elastic yarns 847, 848 (before cut) are arranged in the crossing area 849, at an angle which is equal to or larger than 45 degrees and equal to or smaller than 135 degrees, to thereby cut the elastic yarns 847, 848 more reliably. Further, the angle is equal to or larger than 80 degrees and equal to or smaller than 100 degrees and it is possible to cut the elastic yarns 847, 848 more reliably.

The plurality of second cutting blades 9175 are arranged in the rotating blade 9171 so that the second cutting blades 9175 are tilted relatively to the second direction where each inclined part 8443 of the elastic yarns 844 (before cut) is positioned in the crossing area 849, at an angle which is equal to or larger than 45 degrees and equal to or smaller than 135 degrees, to thereby cut the elastic yarns 844 more reliably. Further, the angle is equal to or larger than 80 degrees and equal to or smaller than 100 degrees and it is possible to cut the elastic yarns 844 more reliably.

In the rotating blade 9171 of the elastic member cutting part 917, the plurality of first cutting blades 9174 and the plurality of second cutting blades 9175 are almost uniformly distributed in the areas where the first cutting blades 9174 and the second cutting blades 9175 are provided. With this operation, the first cutting lines 4441 and the second cutting lines 4442 are uniformly distributed and formed in the crossing area 849 (i.e., the non-contracted part 49). As a result, both of the elastic yarns 847, 848 and the elastic yarns 844 can be cut at a plurality of positions more reliably.

In the above manufacturing apparatus 9, since the direction where the first middle elastic member 47 and the second middle elastic member 48 are positioned is parallel to the transfer direction of the first sheet member 841 and the second sheet member 842, it is possible to easily arrange the elastic yarns 847, 848 between the both sheet members and to easily manufacture the outer covering sheet 4 and the absorbent product 1.

Figure 10:
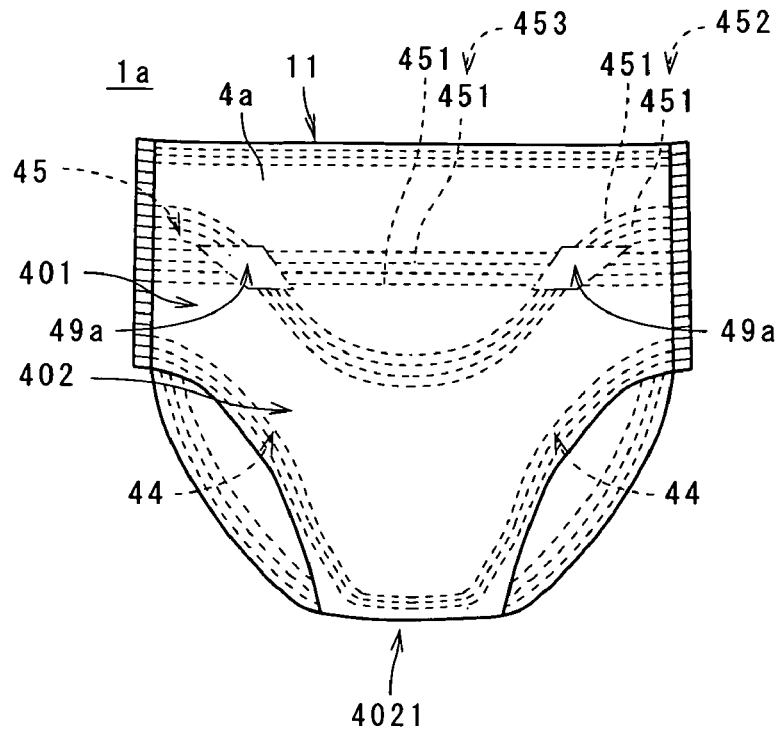
FIG. 10 is a front view of an absorbent product in accordance with the second preferred embodiment.

Next, discussion will be made on an absorbent product in accordance with the second preferred embodiment of the present invention. FIG. 10 is a front view of an absorbent product 1a in accordance with the second preferred embodiment. In an outer covering sheet 4a of the absorbent product 1a, out of a plurality of elastic yarns 451 (eight in the preferred embodiment) included in a front elastic member 45, upper four elastic yarns 451 bend toward the lower side (i.e., toward a folded part 4021) in the vicinity of the central portion in the horizontal direction of the absorbent product 1a, and a lower end of a bent portion of the upper four elastic yarns 451 is located below the lowest elastic yarn 451, as shown in FIG. 10. In the outer covering sheet 4a, a first middle elastic member and a second middle elastic member are not provided in a middle part 402 and non-contracted parts are not provided on leg elastic members 44. The other constituent elements are the same as those in the absorbent product 1 shown in FIGS. 1 to 5 and represented by the same reference signs.

As shown in FIG. 10, non-contracted parts 49a in the outer covering sheet 4a are overlapping areas of the upper four elastic yarns 451 (hereinafter, referred to as "upper elastic yarn group 452") included in the front elastic member 45 and lower four elastic yarns 451 (hereinafter, referred to as "lower elastic yarn group 453") included in the front elastic member 45. The non-contracted parts 49a are surrounded by double-dash lines in FIG. 10 (the same is applied to FIGS. 11 and 12).

In the outer covering sheet 4a of the absorbent product 1a, since the upper elastic yarn group 452 included in the front middle elastic member 45 bend toward the folded part 4021 in the middle part 402, it is possible to fit a portion close to the middle part 402 of the front part 401 to the vicinity of wearer's crotch on a stomach side of the wearer. Since the crossing areas of the upper elastic yarn group 452 and the lower elastic yarn group 453 are the non-contracted parts 49a, flexibility of the front part 401 in the outer covering sheet 4a is improved and the wearer is provided with comfortable feeling in wearing the absorbent product 1a. In a case where the non-contracted parts 49a overlap with the absorbent 2 (see FIG. 4), it is possible to prevent occurrence of damage such as twist of the absorbent 2 caused by overlapping the absorbent 2 with the crossing areas of the elastic members.

Manufacturing processes of the absorbent product 1a are almost same as those in the first preferred embodiment except that elastic yarns cut in Step S13 of FIG. 9 are different. In manufacturing of the absorbent product 1a, extended elastic yarns to be the upper elastic yarn group 452 and extended elastic yarns to be the lower elastic yarn group 453 are bonded between the first sheet member 841 and the second sheet member 842 (see FIG. 8A) with crossing each other, the above elastic yarns are cut in crossing areas of the elastic yarns by the plurality of cutting blades including the first cutting blades tilted relatively to a direction where the elastic yarns to be the upper elastic yarn group 452 are arranged and the second cutting blades tilted relatively to a direction where the elastic yarns to be the lower elastic yarn group 453 are arranged, and thereby the crossing areas become the non-contracted parts 49a.

In manufacturing of the absorbent product 1a according to the second preferred embodiment, since the plurality of elastic yarns can be simultaneously and reliably cut in the crossing areas of the elastic yarns, it is possible to maintain elasticity in a required portion and to easily form the outer covering sheet 4a with high flexibility, similarly to the first preferred embodiment.

Figure 11:
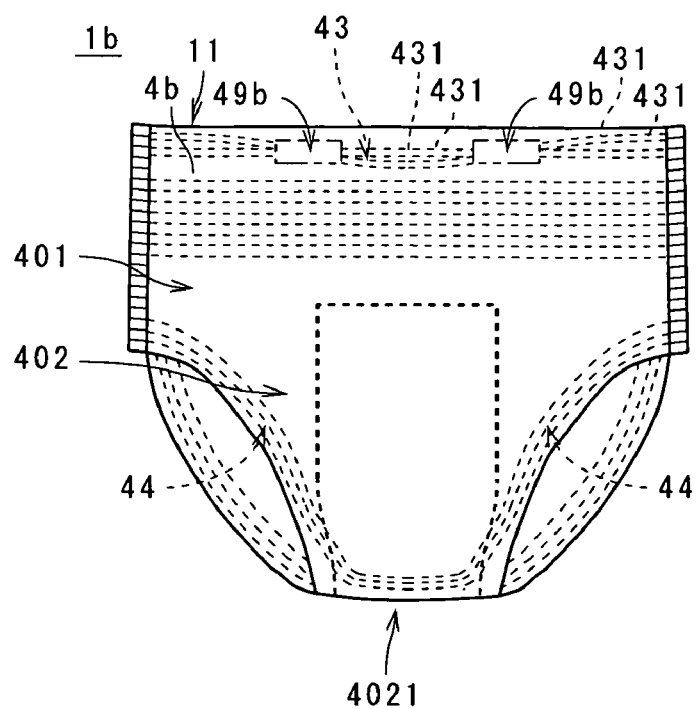
FIG. 11 is a front view of an absorbent product in accordance with the third preferred embodiment.

Next discussion will be made on an absorbent product in accordance with the third preferred embodiment of the present invention. FIG. 11 is a front view of an absorbent product 1b in accordance with the third preferred embodiment. In an outer covering sheet 4b of the absorbent product 1b, a waist elastic member 43 has a plurality of elastic yarns 431 (four in the preferred embodiment), upper two elastic yarns 431 out of the elastic yarns 431 bend toward the lower side in the vicinity of the central portion in the horizontal direction of the absorbent product 1b, and a lower end of a bent portion of the upper two elastic yarns 431 is located below the lowest elastic yarn 431, as shown in FIG. 11. In the outer covering sheet 4b, a first middle elastic member and a second middle elastic member are not provided in a middle part 402 and non-contracted parts are not provided on leg elastic members 44. The other constituent elements are the same as those in the absorbent product 1 shown in FIGS. 1 to 5 and represented by the same reference signs.

As shown in FIG. 11, non-contracted parts 49b in the outer covering sheet 4b are crossing areas of the upper two elastic yarns 431 included in the waist elastic member 43 and lower two elastic yarns 431 included in the waist elastic member 43. With this operation, it is possible to improve flexibility of a portion close to the waist opening 11 in the front part 401 of the outer covering sheet 4b and to provide the wearer with comfortable feeling in wearing the absorbent product 1b.

Manufacturing processes of the absorbent product 1b are almost same as those in the first preferred embodiment except that elastic yarns cut in Step S13 of FIG. 9 are different. In the method, since the plurality of elastic yarns 431 crossing in the crossing areas can be simultaneously and reliably cut by the plurality of cutting blades including the first cutting blades and the second cutting blades whose orientations are different from each other, it is possible to maintain elasticity in a required portion and to easily form the outer covering sheet 4b with high flexibility.

Figure 12:
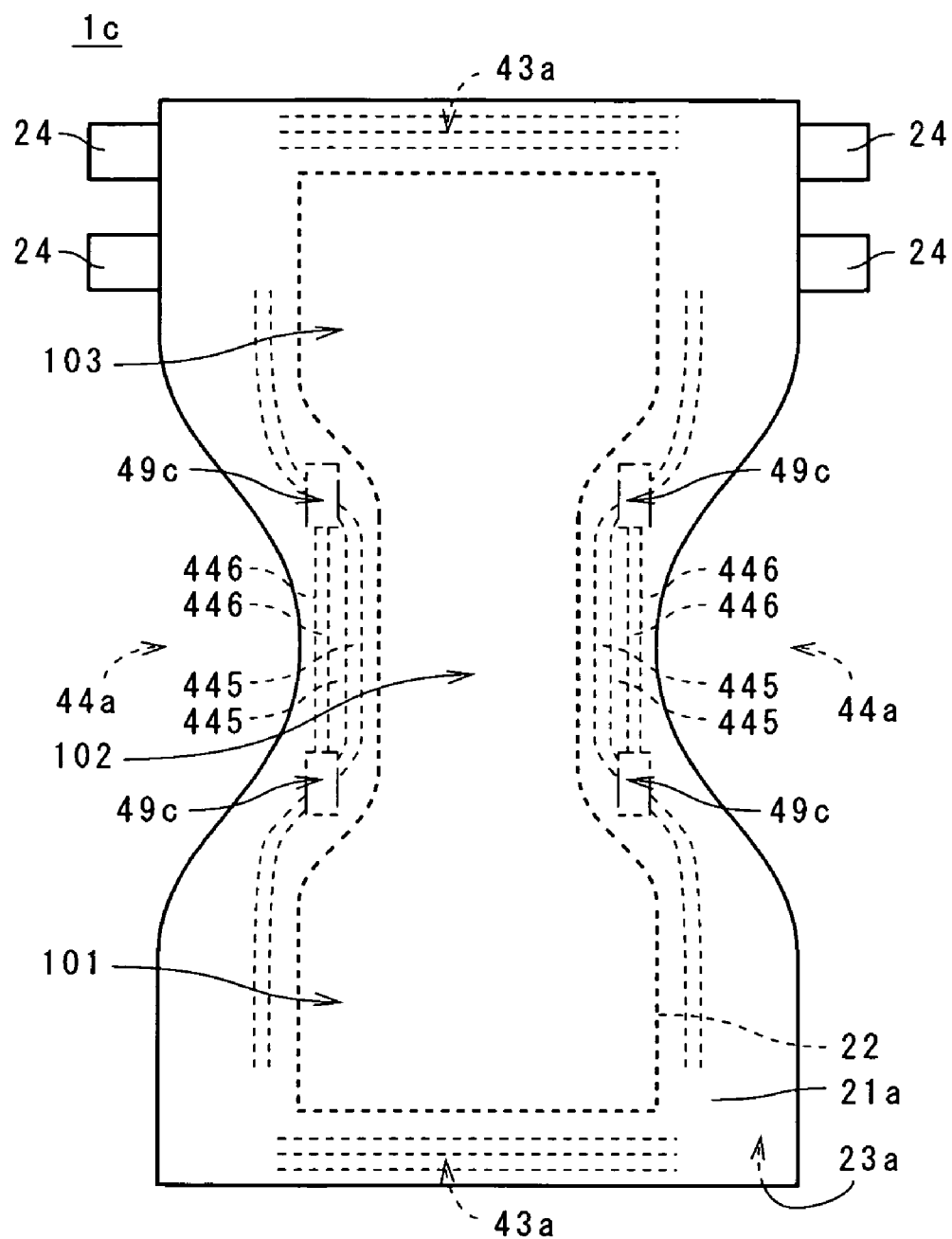
FIG. 12 is a plan view of an absorbent product in accordance with the fourth preferred embodiment in a state where the absorbent product is spread.

Next discussion will be made on an absorbent product in accordance with the fourth preferred embodiment of the present invention. FIG. 12 is a plan view of an absorbent product 1c in accordance with the fourth preferred embodiment in a state where the absorbent product 1c is spread. The absorbent product 1c is a so-called open-type disposal diaper, and a front part 101 located on a stomach side of a wearer and a back part 103 located on a back side of the wearer are fastened around waistline of the wearer by using fastening tapes 24 in wearing the absorbent product 1c.

The absorbent product 1c has an absorbent core 22, a top sheet 21a covering an upper surface of the absorbent core 22 (i.e., one main surface on an inner side of the absorbent core 22), a back sheet 23a covering a lower surface of the absorbent core 22 (i.e., the other main surface of the absorbent core 22), and the top sheet 21a and the back sheet 23a are bonded around the absorbent core 22 by the hot melt adhesive. As shown in FIG. 12, in a state where the absorbent product 1c is expanded, widths in the horizontal direction of the front part 101 and the back part 103 in the top sheet 21a and the back sheet 23a are almost equal, and a width of a middle part 102 between the front part 101 and the back part 103 is smaller than that of the front part 101 and the back part 103. In other words, each of the top sheet 21a and the back sheet 23a is formed in a form of hourglass.

The absorbent product 1c has an extended waist elastic member 43a which is bonded between the top sheet 21a and the back sheet 23a on both sides in a longitudinal direction of the absorbent core 22 (the longitudinal direction is a direction perpendicular to the horizontal direction and corresponds to the vertical direction in FIG. 12) and contracts to form waist opening gathers, and an extended pair of leg elastic members 44a which are bonded between the top sheet 21a and the back sheet 23a on right and left sides of the hourglass absorbent core 22 and contract to form a pair of leg opening gathers. In other words, a bonded body of the top sheet 21a and the back sheet 23a to which the above elastic members are bonded is an elastic sheet which is a part of the absorbent product 1c.

Each leg elastic member 44a has two elastic yarns 445 which are arranged so as to bend along an edge of the middle part 102, the edge bending toward the internal portion in the horizontal direction of the absorbent product 1c, and two elastic yarns 446 which are linearly arranged in parallel with the longitudinal direction. In manufacturing of the absorbent product 1c, the elastic yarns 445 and the elastic yarns 446 are cut in crossing areas of these elastic yarns similarly to the first preferred embodiment, and the crossing areas become non-contracted parts 49c. Similarly to the first to third preferred embodiments, it is possible to easily form an elastic sheet (i.e., the bonded body of the top sheet 21a and the back sheet 23a) which maintains elasticity in a required portion and has high flexibility.

Though the preferred embodiments of the present invention have been discussed above, the present invention is not limited to the above-discussed preferred embodiments, but allows various variations.

In the absorbent product 1 according to the first preferred embodiment, all elastic yarns included in the first middle elastic member 47 and the second middle elastic member 48 are cut in the crossing areas to be the non-contracted parts 49, but for example, out of the three first middle elastic yarns 471 included in the first middle elastic member 47, only two first middle elastic yarns 471 may be cut with the three elastic yarns 441 included in the leg elastic members 44 to form the non-contracted parts 49.

In the above absorbent product 1, the first middle elastic yarns 471 and the second middle elastic yarns 481 included in the first middle elastic member 47 and the second middle elastic member 48 are not necessarily arranged in nearly parallel with the horizontal direction, as long as the first middle elastic yarns 471 and the second middle elastic yarns 481 are arranged along the horizontal direction. For example, the first middle elastic yarns 471 and the second middle elastic yarns 481 may be arranged so as to curve toward the folded part 4021 of the middle part 402 in the vicinity of the central portion in the horizontal direction. One of the first middle elastic member 47 and the second middle elastic member 48 may be provided in the middle part 402 of the outer covering sheet 4 in the absorbent product 1. In this case, the middle gathers and the pair of non-contracted parts 49 are formed in one of the middle front part 4022 and the middle back part 4023.

In the absorbent product 1a according to the second preferred embodiment, the upper elastic yarn group 452 and the lower elastic yarn group 453 in the front elastic member 45 are cut in the crossing areas of these elastic yarn groups to form the non-contracted parts 49a on the front elastic member 45, but a back elastic member 46 may be the same shape as the front elastic member 45 or only the back elastic member 46 may be the above shape. Also in the absorbent product 1b according to the third preferred embodiment, there may be a case where the non-contracted parts 49b are provided on the waist elastic member 43 in each of the front part 401 and the back part 403 or the non-contracted parts 49b are provided on one of the waist elastic members 43 provided in the front part 401 and the back part 403.

As discussed above, in the absorbent products according to the first to third preferred embodiments, elastic members are cut in crossing areas of two elastic members out of the waist elastic member 43, the leg elastic members 44, the front elastic member 45, the back elastic member 46, the first middle elastic member 47 and the second middle elastic member 48, to form non-contracted parts, or an elastic member is cut in crossing areas of a plurality of elastic yarns included in one of the above elastic members, to form non-contracted parts. Non-contracted parts may be formed by cutting elastic members in crossing areas of one of the above elastic members and an elastic member other than the above elastic members.

The non-contracted parts in the absorbent product do not need to completely lose elasticity but may be portions which have a smaller elasticity and are substantially regarded as not having elasticity as compared with the other portions with elasticity where elastic members are located in the outer covering sheet (e.g., portions where the leg opening gathers are formed).

In manufacturing of the absorbent products according to the first to third preferred embodiments, the elastic yarns cut in the crossing areas are not necessarily cut with the first sheet 41 and the second sheet 42 but may be cut with at least one of the first sheet 41 and the second sheet 42. In other words, at least one of the first sheet 41 and the second sheet 42 has a plurality of cutting lines in the outer covering sheet of the absorbent product. In manufacturing of the absorbent product 1c according to the fourth preferred embodiment, the elastic yarns cut in the crossing areas are not necessarily cut with the top sheet 21a and the back sheet 23a but may be cut with at least one of the top sheet 21a and the back sheet 23a. Thus, it is possible to easily form the absorbent product.

In the absorbent products according to the above preferred embodiments, the elastic member cut in the crossing area may have only one elastic yarn, or may have two or four elastic yarns or more.

In manufacturing of the absorbent product 1 according to the first preferred embodiment, the first cutting blades 9174 and the second cutting blades 9175 are not necessarily uniformly arranged in the elastic member cutting part 917 of the manufacturing apparatus 9. For example, in an outer surface of the rotating blade 9171, the plurality of second cutting blades 9175 are arranged in an area, and the plurality of first cutting blades 9174 are arranged on both sides in a circumferential direction of the area (i.e., the both sides are a front part and a back part in the rotation direction of the rotating blade 9171), to form a plurality of cutting blade groups corresponding to one non-contracted part 49. The plurality of second cutting blades 9175 may be arranged on both sides in a circumferential direction of an area where the plurality of first cutting blades 9174 are arranged.

The plurality of cutting blades corresponding to one non-contracted part 49 may be, for example, a group of one type of cutting blades arranged in a direction which is tilted relatively to the direction (i.e., transfer direction) where the first middle elastic member 47 and the second middle elastic member 48 are positioned and the direction where the inclined part 443 of the leg elastic members 44 is positioned. That is, the orientations of the first cutting blades 9174 may be the same as those of the second cutting blades 9175. In a case where the orientations of the first cutting blades 9174 are different from those of the second cutting blades 9175, the first cutting blades 9174 may be arranged in a direction parallel to the inclined part 443 of the leg elastic members 44, and the second cutting blades 9175 may be arranged in a direction parallel to the direction where the first middle elastic member 47 and the second middle elastic member 48 are positioned.

In manufacturing of the above absorbent product, adhesive may be applied to one of the first sheet member 841 and the second sheet member 842 in Step S11 of FIG. 9. Cutting of elastic yarns (Step S13) is not necessarily performed before bonding of the absorbent 2 to the outer covering sheet member 84 (Step S14), as long as cutting of elastic yarns (Step S13) is performed after bonding of the first sheet member 841 and the second sheet member 842 (Step S12).

In the first to third preferred embodiments, though the whole (or a part of the) outer covering sheet 4 in the absorbent product 1 is an elastic sheet having the non-contracted parts which are formed by cutting the elastic member in the crossing areas, only a part of the outer covering sheet 4 in the absorbent product 1 may be formed by an elastic sheet which is separately formed. In other words, the outer covering sheet 4 includes an elastic sheet having the non-contracted parts which are formed by cutting the elastic member in the crossing areas.

For example, the elastic sheet may be used as the side wall parts 3 in the absorbent 2 of the absorbent product 1 according to the first preferred embodiment. In this case, standing gathers which come into contact with the vicinity of wearer's crotch in wearing are formed by contracting the elastic sheet. In the elastic sheet, the first sheet and the second sheet are not necessarily separate sheets, but there may be a case where one sheet-like member is folded into two and an elastic member is bonded between portions on both sides of a fold line. In this case, a portion on one side of the fold line in the sheet-like member and a portion on the other side of the fold line are the first sheet and the second sheet.

The elastic sheet may be used for auxiliary absorbent pads such as a urine absorbing pad which is attached on an inner side of a disposal diaper or the like or various absorbent products.

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2007-143495 filed in the Japan Patent Office on May 30, 2007, the entire disclosure of which is incorporated herein by reference.

What is claimed is:

1. A method of manufacturing an elastic sheet for an absorbent product which receives excrement from a wearer, the method comprising:
    positioning an extended first elastic member along a first direction on a first sheet member;
    positioning an extended second elastic member along a second direction tilted relative to the first direction such that the second elastic member crosses the first elastic member at a crossing area;
    after said positioning operations, laminating a second sheet member on the first sheet member such that the first elastic member and the second elastic member are interposed between the first sheet member and the second sheet member, and bonding the first sheet member and the second sheet member together; and
    after said laminating operation, cutting the first elastic member and the second elastic member, together with at least one of the first sheet member and the second sheet member, at the crossing area using cutting blades,
    wherein the cutting blades include a plurality of first cutting blades tilted relative to the first direction and a plurality of second cutting blades tilted relative to the second direction,
    wherein said cutting operation includes forming a plurality of cuts in the crossing area with the plurality of first cutting blades and the plurality of second cutting blades, and
    wherein the first elastic member has a plurality of first elastic yarns along the first direction, the second elastic member has a plurality of second elastic yarns along the second direction, and
    wherein one of the second elastic yarns is disposed directly over one of the first elastic yarns at a crossing point, and the cutting operation includes cutting the second elastic member and the first elastic member at the crossing point.

2. The method according to claim 1, wherein the plurality first cutting blades are tilted relative to the first direction at an angle which is at least 45 degrees and not more than 135 degrees, and
    wherein the plurality of second cutting blades are tilted relative to the second direction at an angle which is at least 45 degrees and not more than 135 degrees.

3. The method according to claim 2, wherein the plurality of cuts formed in said cutting operation are uniformly distributed in the crossing area.

4. The method according to claim 1, wherein the plurality of first cutting blades are tilted relative to the first direction at an angle which is at least 80 degrees and not more than 100 degrees, and
    wherein the plurality of second cutting blades are tilted relative to the second direction at an angle which is at least 80 degrees and not more than 100 degrees.

5. The method according to claim 4, wherein the plurality of cuts formed in said cutting operation are uniformly distributed in the crossing area.

6. The method according to claim 1, further comprising transferring the first sheet member in a transfer direction, wherein the first direction is parallel to the transfer direction.

7. The method according to claim 1, wherein the cuts are a plurality of discrete incisions.

* * * * *